US011483471B2

(12) United States Patent
Scheiner et al.

(10) Patent No.: US 11,483,471 B2
(45) Date of Patent: Oct. 25, 2022

(54) INSPECTION SYSTEM FOR USE IN MONITORING PLANTS IN PLANT GROWTH AREAS

(71) Applicant: VIEWNETIC LTD., Tel Aviv (IL)

(72) Inventors: David Scheiner, Savyion (IL); Eilat Tal, D.N. Arava (IL); Hai Benron, Haifa (IL)

(73) Assignee: Viewnetic Ltd., Tel Aviv (IL)

( * ) Notice: Subject to any disclaimer, the term of this patent is extended or adjusted under 35 U.S.C. 154(b) by 0 days.

(21) Appl. No.: 17/274,567

(22) PCT Filed: Sep. 9, 2019

(86) PCT No.: PCT/IL2019/051006
§ 371 (c)(1),
(2) Date: Mar. 9, 2021

(87) PCT Pub. No.: WO2020/049575
PCT Pub. Date: Mar. 12, 2020

(65) Prior Publication Data
US 2022/0050093 A1 Feb. 17, 2022

Related U.S. Application Data

(60) Provisional application No. 62/728,815, filed on Sep. 9, 2018.

(51) Int. Cl.
*H04N 5/232* (2006.01)
*A01M 7/00* (2006.01)
(Continued)

(52) U.S. Cl.
CPC .......... *H04N 5/23218* (2018.08); *A01G 7/00* (2013.01); *A01M 7/0089* (2013.01);
(Continued)

(58) Field of Classification Search
CPC .......... H04N 5/23218; H04N 5/23299; H04N 5/247; H04N 5/2354; G01N 2021/8466;
(Continued)

(56) References Cited

U.S. PATENT DOCUMENTS

2007/0153114 A1* 7/2007 Ueda ............... H04N 5/232123
348/E5.04
2009/0160951 A1 6/2009 Anderson et al.
(Continued)

FOREIGN PATENT DOCUMENTS

EP  3171327 A  5/2017
WO 2014/106814 A2 7/2014
(Continued)

OTHER PUBLICATIONS

David E Jacobs et al: "Focal Stack Compositing for Depth of Field Control", Jan. 31, 2012.
(Continued)

*Primary Examiner* — Kathleen V Nguyen
(74) *Attorney, Agent, or Firm* — Browdy and Neimark, P.L.L.C.

(57) ABSTRACT

An inspection system is presented for use in monitoring plants' conditions in a plant growing area. The inspection system comprises: an optical probe comprising at least one imaging set, each imaging set comprising: a flash illuminator unit; an imaging unit configured with a predetermined resolution; and a sensing unit; the optical probe being configured and operable to perform one or more imaging sessions on a target in a plant growing area at a target location during a movement of the optical probe along a movement path in a vicinity of the target location, said sensing unit comprising a distance sensing element configured and operable to determine an instantaneous distance between the imaging unit and the target being imaged, and
(Continued)

generate distance sensing data indicative thereof; and a control unit configured and operable to be responsive to the distance sensing data to initiate the imaging session and synchronize operation of the flash illuminator unit and the imaging unit to capture images of the target by the optical probe, thereby enabling analyzing the images and determining a condition of the target being indicative of at least one of pest, insect and disease presence at the target.

31 Claims, 16 Drawing Sheets

(51) Int. Cl.
| | |
|---|---|
| *B64C 39/02* | (2006.01) |
| *G01B 11/24* | (2006.01) |
| *G01N 21/31* | (2006.01) |
| *G01N 21/84* | (2006.01) |
| *G01N 33/00* | (2006.01) |
| *H04N 5/247* | (2006.01) |
| *A01G 7/00* | (2006.01) |
| *H04N 5/235* | (2006.01) |
| *H04N 7/18* | (2006.01) |

(52) U.S. Cl.
CPC ............ *B64C 39/024* (2013.01); *G01B 11/24* (2013.01); *G01N 21/31* (2013.01); *G01N 21/84* (2013.01); *G01N 33/0098* (2013.01); *H04N 5/2354* (2013.01); *H04N 5/23299* (2018.08); *H04N 5/247* (2013.01); *H04N 7/188* (2013.01); *B64C 2201/123* (2013.01); *G01N 2021/8466* (2013.01)

(58) Field of Classification Search
CPC ... G01N 2021/0221; G01N 2021/8416; G01N 2021/252; G01N 21/84; G01N 21/31
See application file for complete search history.

(56) References Cited

U.S. PATENT DOCUMENTS

| | | |
|---|---|---|
| 2015/0178546 A1 | 6/2015 | Abramovich et al. |
| 2017/0118925 A1* | 5/2017 | Noguchi .................. G01J 3/42 |
| 2017/0192226 A1 | 7/2017 | Eineren et al. |

FOREIGN PATENT DOCUMENTS

| | | |
|---|---|---|
| WO | 2016/124950 A1 | 8/2016 |
| WO | 2017/066927 A1 | 4/2017 |

OTHER PUBLICATIONS

Feris R et al: "Specular reflection reduction with multi-flash imaging", Computer Graphic and Image Processing, 2004, Proceeding 17th Brazil IAN Symposium on Curitiba, PR, Brazil Oct. 17-20, 2004, pp. 3160321.

* cited by examiner

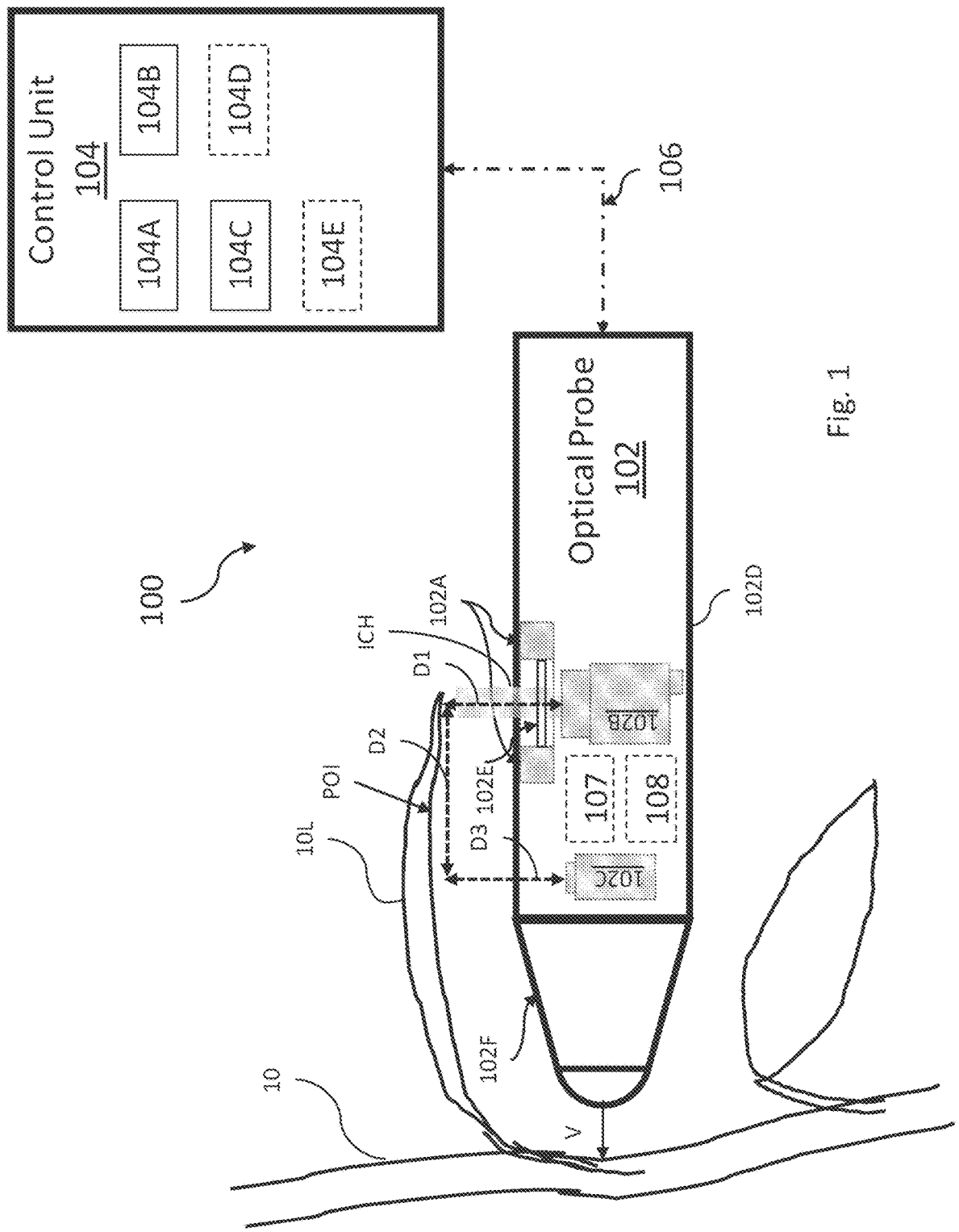

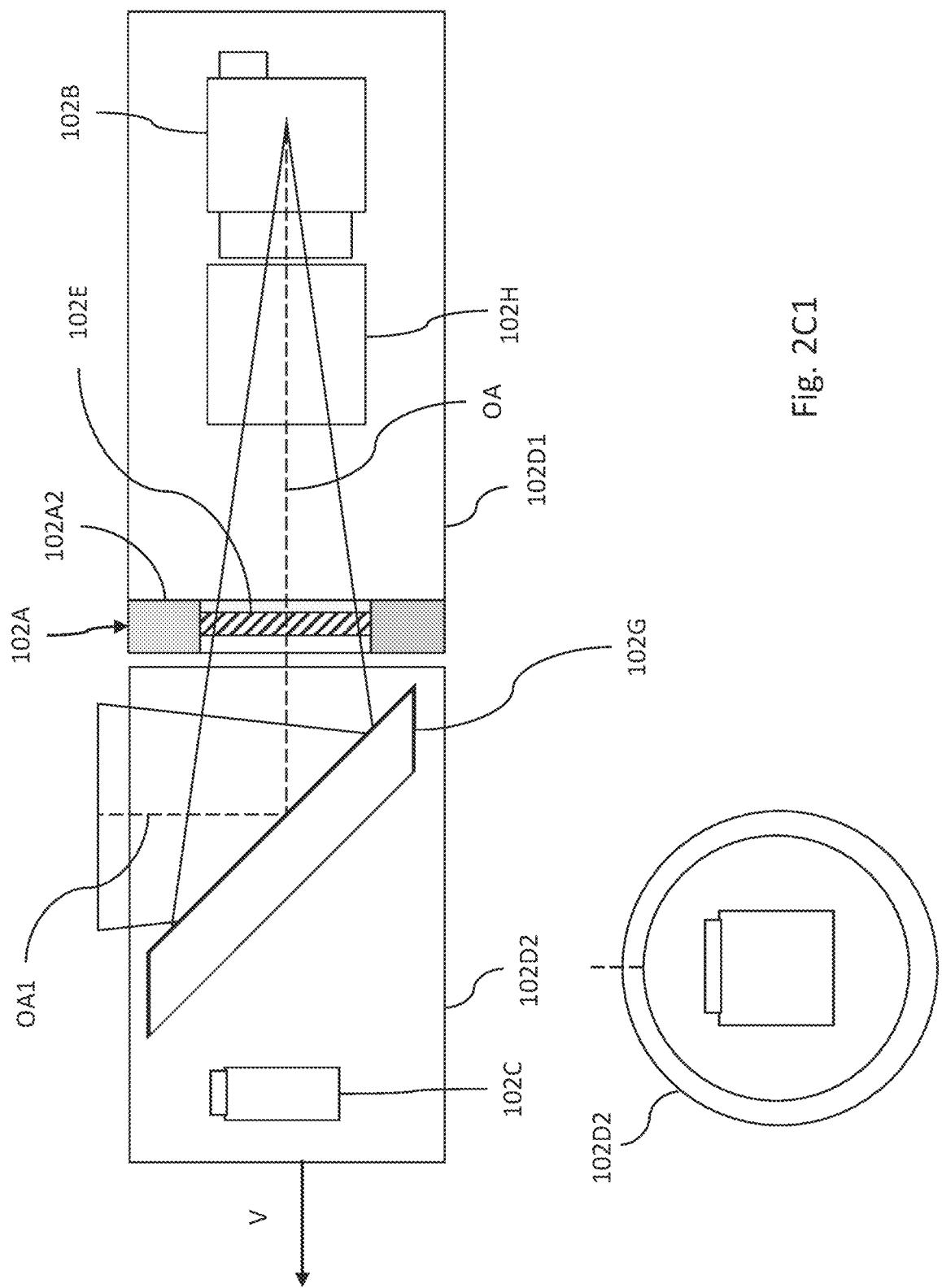
Fig. 2C1

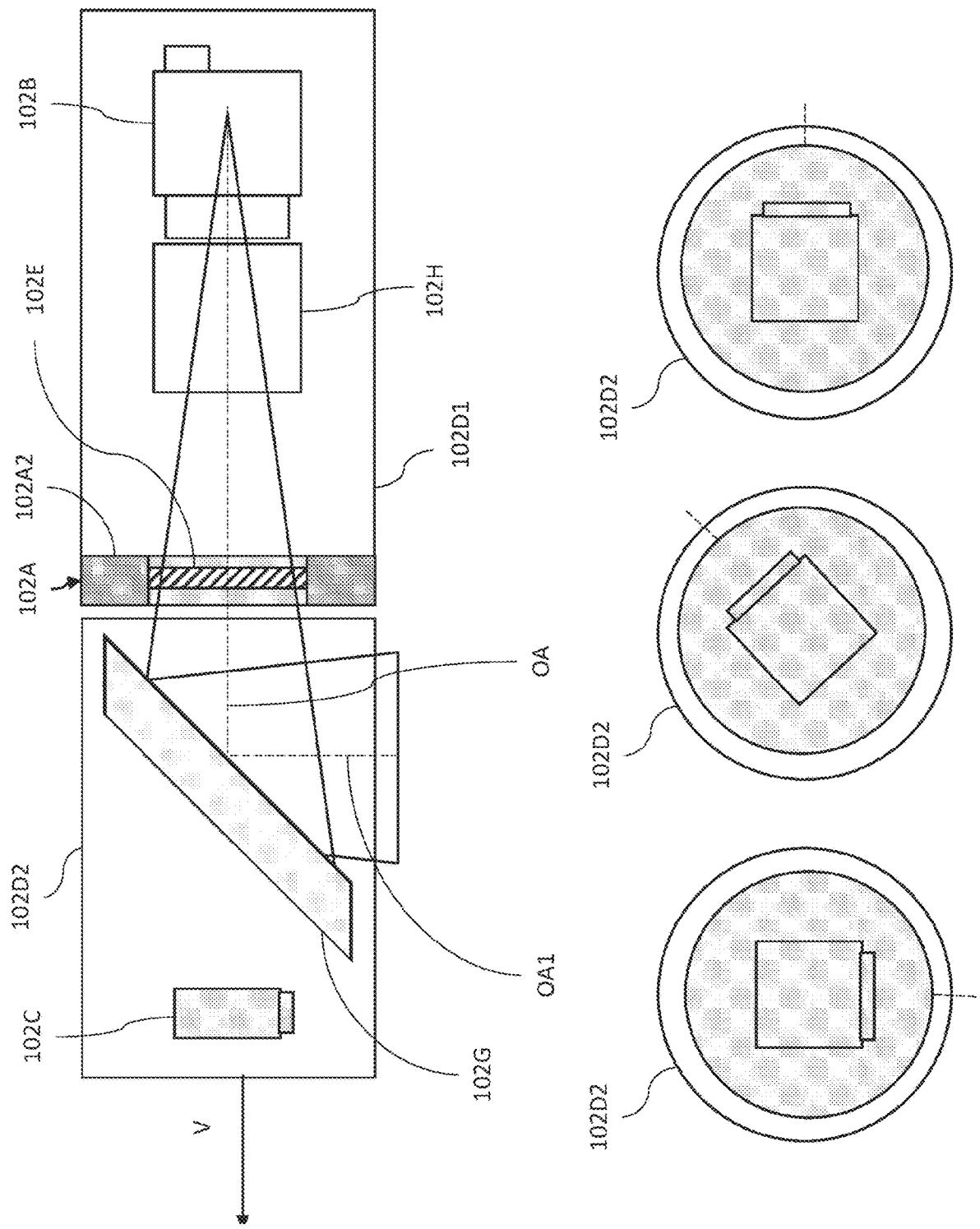

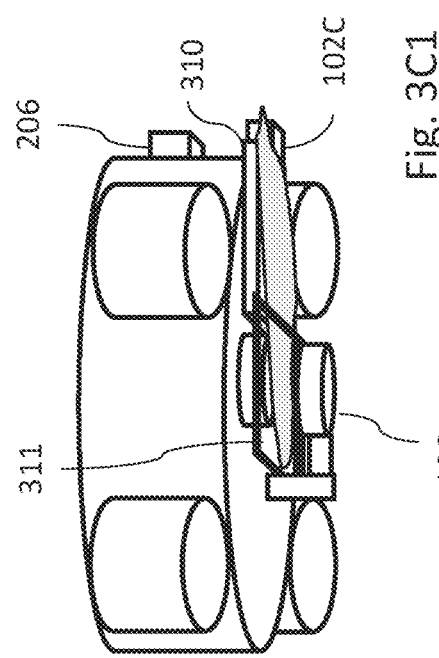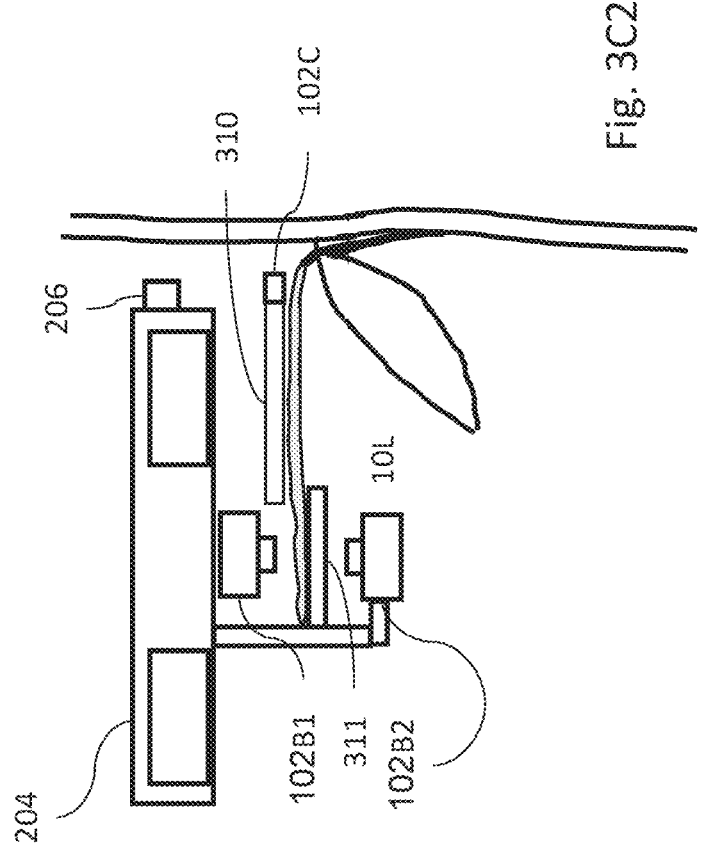

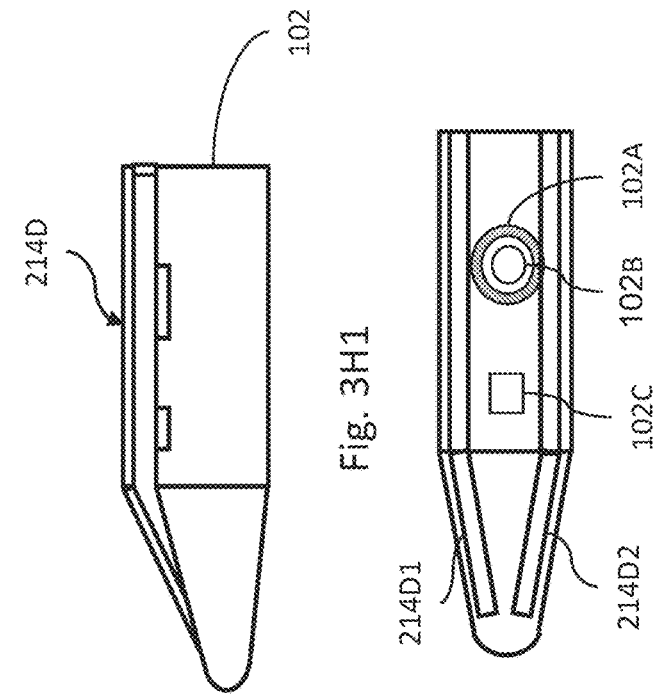
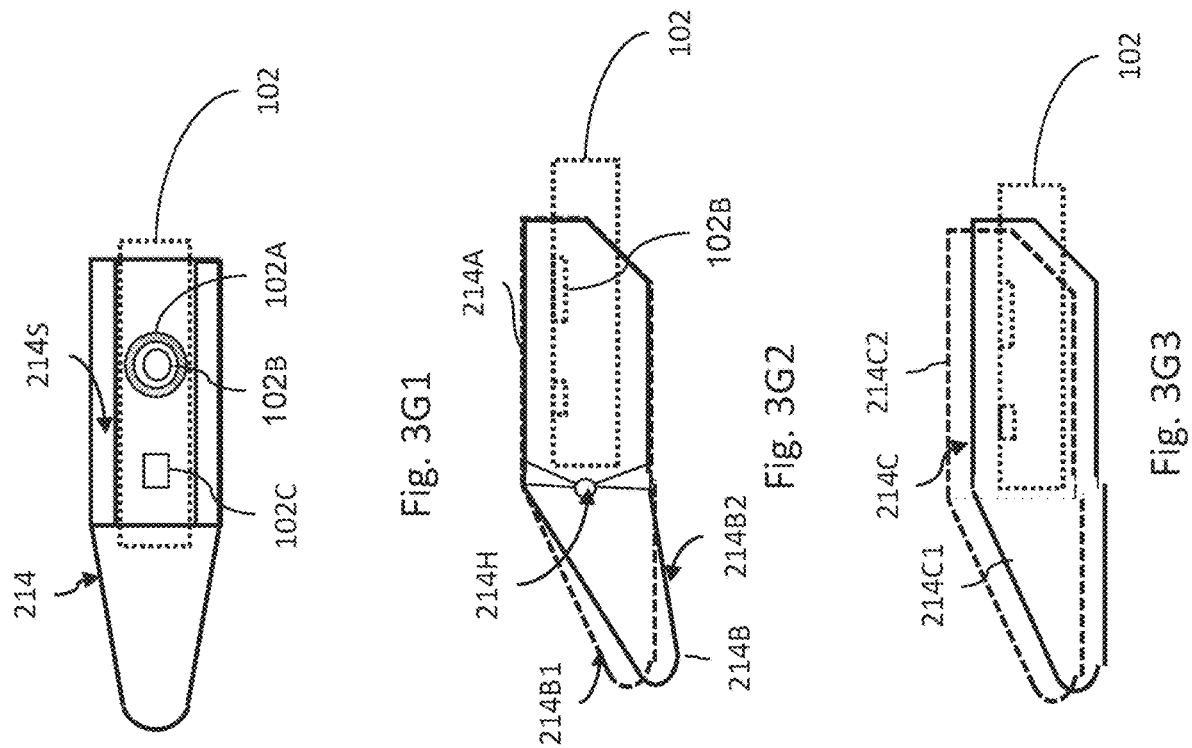

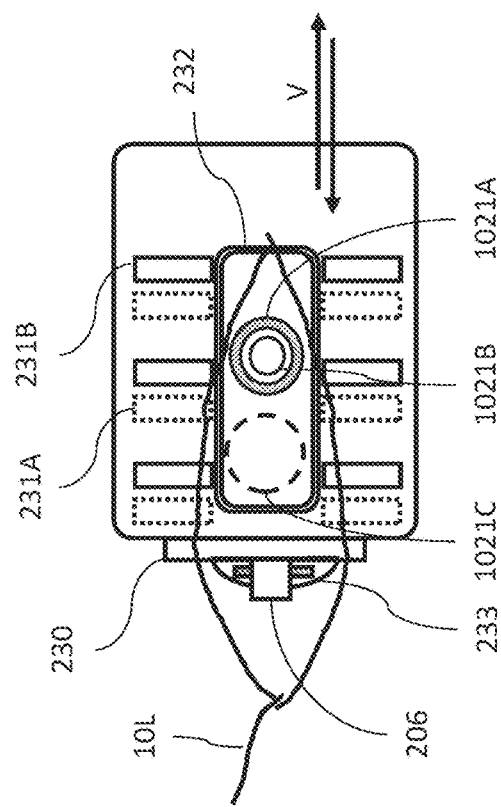
Fig. 4C2
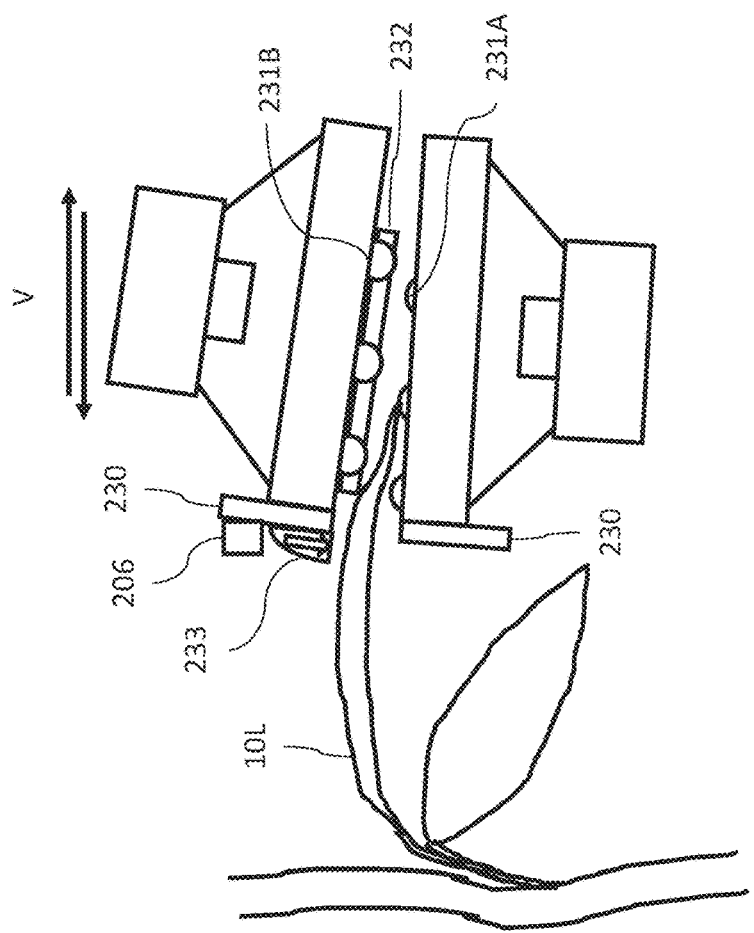
Fig. 4C1

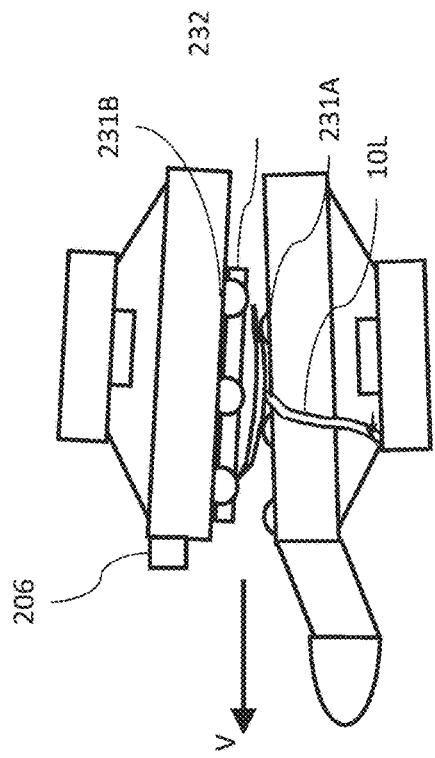
Fig. 4D2
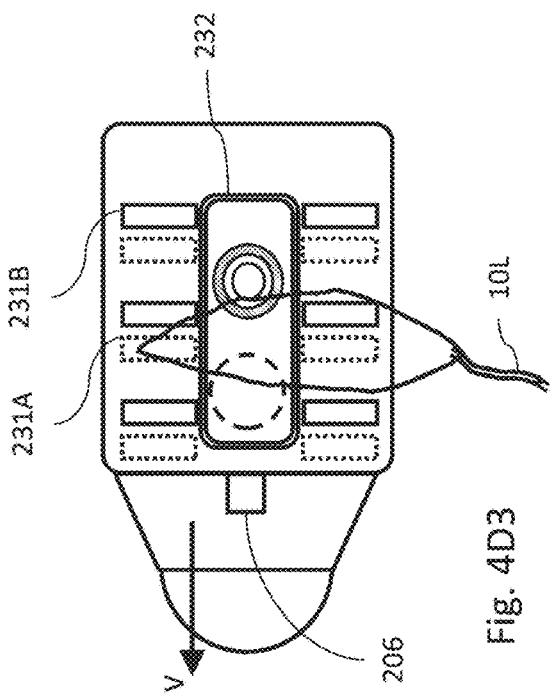
Fig. 4D3
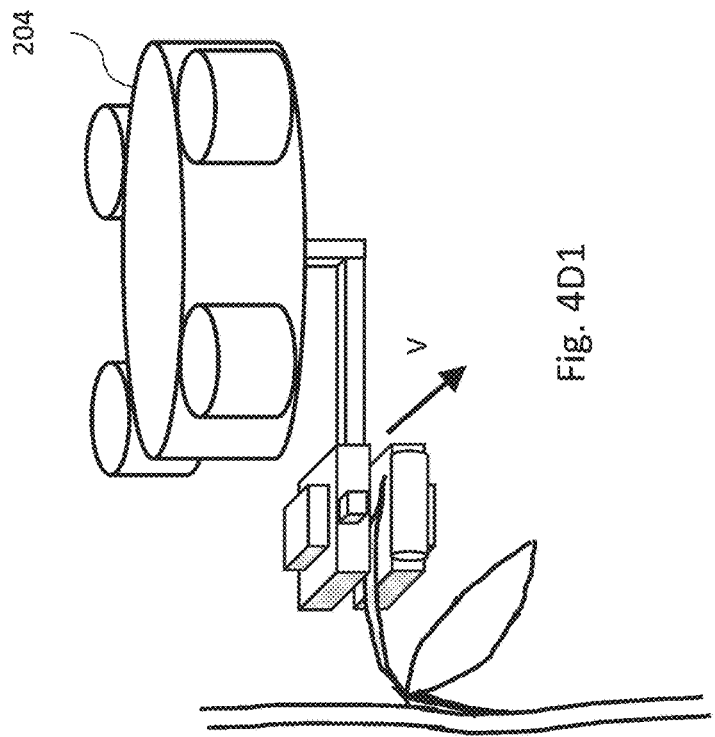
Fig. 4D1

INSPECTION SYSTEM FOR USE IN MONITORING PLANTS IN PLANT GROWTH AREAS

TECHNOLOGICAL FIELD

The invention relates generally to the agricultural field, and more specifically to automated systems and methods of monitoring of plants and/or plant treatment decision making in plant growth areas.

BACKGROUND

Crops require a lot of care, either when grown in protected environment (such as in a greenhouse) or outdoors, especially when cultivated on a large scale where farmers continuously face a variety of challenges, including the need to maintain plants' health over the whole plant life cycle, control flower pollination, and insure healthy as well as good yield crops. Indeed, it can be a difficult task to know whether the crop, at a specific time point, suffers from a problem, such as existence of pest, disease, or nutritional deficit, and what is the extent of the problem until it is readily visible. Often by that stage, it may require expensive and extensive intervention. Crop yield is affected by the physiological performance of the crop throughout its development cycle. Precise intervention at critical developmental stages, allows farmers to achieve high yields of the crop. A common practice for monitoring crops for pests, diseases and other deleterious conditions, has been the use of human scouts who visually inspect the crop. However, human inspection might take a long time, especially in large plant areas, and might facilitate the spread of those pests and diseases, for example, through physical contact with multiple plants, and is subject to subjective interpretation of the inspecting person.

Many crop management practices are employed based on past practices and outcome. A common underlying assumption is that crops are uniform and perform evenly which is not necessarily the case.

Sensor systems have been developed for crop monitoring. For example, some systems use a grid of sensors suspended above the crop or which fly over the crops. Handheld devices are also used to capture data from individual plants. Other systems rely on visual detection by means of motion detection or visual pattern recognition.

Some sensor systems are directed toward specific indicators (presence of disease, emergence of pests, etc.) with narrow spectra of responses. For example, fluorescent measurement systems have been used to detect far red spectra produced by plants when exposed to blue or red light. Conventional fluorescent measurement requires complex equipment, and typically a single assessment takes several minutes. Other sensory systems can collect very general information (temperature, humidity) that cannot accurately pinpoint problems at the level of individual plants.

General Description

The present invention provides novel systems and methods for use in target inspection applications, which is particularly useful for management of crops, for example in greenhouses or open fields (herein, plant growth/growing areas). The technique of the invention enables high quality, yet cost effective and time saving, monitoring and management of plant conditions, either manually or autonomously, by utilizing novel techniques for collecting high-resolution characterization data from each plant, plant part or portion of the plant part in a crop area, and individually characterizing and determining the status of each plant, plant part of portion of the plant part, such as existence of disease, pest infestations and detrimental conditions, as well as the growing stage such as flowering and fruitage.

The invention also enables performing analysis of the plant condition and generating corresponding relevant recommendations for interventions. While being capable of managing each individual plant, the invention is particularly useful in managing large/multiple farming areas due to the highly effective data collection and analysis techniques.

The invention provides an inspection system for use in monitoring plants' conditions in a plant growing area. The inspection system comprises an optical probe and a control unit. The optical probe comprises at least one imaging set, each imaging set comprising: a flash illuminator unit; an imaging unit configured with a predetermined resolution; and a sensing unit; the optical probe being configured and operable to perform one or more imaging sessions on a target in a plant growing area at a target location during a movement of the optical probe along a movement path in a vicinity of the target location, said sensing unit comprising a distance sensing element configured and operable to determine an instantaneous distance between the imaging unit and the target being imaged, and generate distance sensing data indicative thereof. The control unit is configured and operable to be responsive to the distance sensing data to initiate the imaging session and synchronize operation of the flash illuminator unit and the imaging unit to capture images of the target by the optical probe, thereby enabling analyzing the images and determining a condition of the target being indicative of at least one of pest, insect and disease presence at the target.

The resolution of the imaging unit is a substantially high resolution, which is defined by a desirably high magnification of the imaging unit. More specifically, such high resolution can be described as a certain relatively high ratio between a pixel size of an imaging detector and a size of a corresponding smallest region in the object plane which is being imaged/projected on said pixel. Hence, for a given pixel matrix of an imaging detector and a given distance from the pixel matrix to the object plane, the higher is the resolution the smaller is the field of view. For example, an object having 0.5 mm in size may require about 30×30 resolved pixels in order to be properly imaged with the desirably high resolution. Therefore an effective resolution of about 17 microns is required. If an imaging sensor with pixels of 3 microns in size is used, and the resolution of the optics, measured for example by line-spread-function or other relevant parameter, is 1.5 camera pixels, then a magnification of about $1/3.8=(3\times1.5)/17$ is required from the object to sensor in order to provide the high-resolution capability.

Thus, the desirably high resolution for the plant imaging and inspection, which can be described by a spatial resolution of the imaging unit in an object plane, is practically in a range of 1-100 microns. Hence, that the term "high-resolution" as referred to in this application is in the micron resolution range, specifically concerning a few microns, a few tens of microns or a few hundreds of microns. The specific choice potentially depends on the objects of interest, e.g. the specific pests or beneficial insects, and can therefore be defined differently between various applications.

Specifically, high-resolution characterization data collected includes one or more of the following, but is not limited to, leaf images, leaf underside images, flower images, plant crown images, fruit images, and plant branch images. Yet more specifically, the images can be of only portions of the above plant parts.

Characterization of the plant condition/status may include one or more of the following, but is not limited to, detection and/or measurement of leaf shape, color, discoloring, leaf orientation and linearity, pest insects, beneficial insects, fungi, insect generated liquid drops, fruit size, fruit location and height from the ground, fruit orientation, fruit shape and fruit color. In addition, one or more of the following can be saved in the system for use upon decision making: irrigation and fertilization data, date of planting, date of last harvest, dates of pruning and others.

Analysis of the plant condition, based on the high-resolution characterization data, can be carried out and may include one or more of the following, but is not limited to, generating information on the growing stage, and on the location and severity of detrimental conditions. The growing stage information may include leaf size, leaf color and leaf density and distribution; flower density and distribution; fruit size, fruit color and fruit density and distribution; branch quantity and density. The detrimental conditions information may include fungus location and severity distribution; insect pest location and severity distribution; leaf deformation and severity distribution.

Analysis output may be in the form of tabular data, density maps of parametric data, maps with embedded data such as photographs, recommended treatment maps such as beneficial type and density for spreading and insecticide type and spraying parameters.

Recommendation data based on the analysis of the high-resolution characterization data may include interventions that may relate to one or more of the following, but is not limited to, insecticide spraying, beneficial spreading, irrigation planning, fertilization planning, fruit pruning, leaf and branch pruning, inspection planning, treatment type for detrimental condition taking into account presence of beneficial species. The recommendations may relate to the whole cultivated area or to local requirements in a subsection of the cultivated area, or to a more than one cultivated area. Interventions/Treatment actions may include insecticide spraying, beneficial biological agent distribution, pruning of leaves and branches, thinning of fruit, and fertilizer spreading.

On one hand, diseases, pests, insects, colorization and other plant conditions can be potentially small in size or have similar properties and as such require high resolution data collection techniques, in the range of microns, to effectively analyze the collected data, distinguish and determine the plant condition. On the other hand, collecting high resolution data can be basically slow because there is a need to stop at multiple locations along the way to be able to capture high resolution images, thus lowering data collection efficiency. Yet further, plants and plant parts can be moving with respect to the data collection module (or vice versa) during data collection, thus causing smearing and reducing image quality. The present invention overcomes all the above-listed shortcomings by enabling fast and high-quality data collection of high-resolution images, thereby enabling effective monitoring of large plant growth areas in optimal time and with high accuracy.

The sensing unit used in the optical probe is located at a predetermined distance before the imaging unit with respect to the movement path of the optical probe.

The imaging unit may be configured and operable to acquire a plurality of images with different focal conditions within a focal range of the imaging unit during said imaging sessions. According to some embodiments, the imaging unit defines a plurality of different imaging channels having said different focal conditions, said distance sensing data being indicative of the distance between each of the imaging channels and the target to be imaged. Alternatively or additionally, the imaging unit may define at least one imaging channel configured with an adaptive focus within said focal range for imaging along said at least one imaging channel, said distance sensing data being indicative of the distance between each of said at least one imaging channel and the target to be imaged. The control unit may thus comprise an image controller configured and operable to determine the focal condition based on said distance sensing data being indicative of the distance between the imaging unit and the target and controllably operate the imaging unit to successively perform the imaging sessions with the different focal conditions.

The imaging unit may define a plurality of different imaging channels, in which case said image controller determines a time sequence of operation of the flash illuminator unit and of the different imaging channels based on one or more of the following: the focal conditions of the imaging channels, the movement of the optical probe, and said distance sensing data being indicative of the distance between each of the imaging channels and the target, to thereby obtain the plurality of images.

In some examples, the image controller is configured to spatially divide the target into one or more sections and allocate one or more imaging channels for imaging each of said one or more sections. For example, the image controller may allocate a number of the imaging channels for imaging each of said one or more sections, such that fields of view of the imaging channels in each section either overlap or are shifted along the movement path of the optical probe, the plurality of images thereby covering the whole target.

In some embodiments, the flash illuminator unit comprises one or more lighting elements associated with each imaging channel defined by the imaging unit. Each lighting element, associated with each imaging channel, is arranged with a different angular orientation with respect to an optical axis of the imaging channel. The control unit determines an angle between the target location and the optical axis of the imaging channel, and selects, for each imaging session, one or more of the lighting elements to provide uniform illumination of the target.

In some embodiments, the control unit further comprises a flash controller configured and operable to control at least one of illumination intensity, illumination angle and illumination time pattern of the flash illuminator unit. The flash controller may be configured and operable to control the at least one of illumination intensity, illumination angle and illumination time pattern of the flash illuminator unit based on one or more of the following: input motion data indicative of the movement path of the optical probe in the vicinity of the target location, number of lighting elements of the flash illuminator unit, distance of a focal plane, exposure time, ambient light, an angle between the target and the flash illuminator unit, reflectivity of target, type of the target, and type of a part of the target being imaged.

The system may further include a movement detection unit configured and operable for providing input motion data to at least one of the control unit, an image controller and a flash controller, for controlling the imaging sessions and a time sequence of operation of the flash illuminator unit and of the different imaging channels.

In some embodiments, the optical probe comprises a housing containing the flash illuminator unit, the imaging unit, and the sensing unit. The housing may comprise a portion thereof formed with a mesh screen comprising an array of features arranged substantially parallel to the movement path of the optical probe, and/or at least one optical window aligned with a respective at least one imaging channel defined by the imaging unit. The imaging of the target can be performed via the mesh screen and/or the optical window.

In some embodiments, the optical probe comprises at least one light directing element associated with a respective at least one imaging channel defined by the imaging unit, for collecting input light from the target and directing collected light to propagate along said imaging channel to a detector of the imaging unit. The lighting element is positioned either upstream or downstream of the light directing element with respect to a direction of propagation of the input light.

In some embodiments, the housing is configured as a two-part device, where a first part accommodates the flash illuminator unit and the imaging unit, and a second part accommodates the light directing element and the sensing unit. The first and second parts of the housing are configured for a relative rotation between them about an axis of the imaging unit.

In some embodiments, the optical probe comprises a plurality of the imaging sets, each imaging set being configured with a field of view of a different angular orientation with respect to an axis of the optical probe.

In some embodiments the system also includes an indication unit configured and operable to provide indication about an operational state of the optical probe.

In some embodiments, the system includes a position controller configured and operable to control one or more of the following: a position of the optical probe, an orientation of the optical probe, an orientation of the movement path of the optical probe with respect to said target location, based on input position data. The position controller may be configured and operable for communication with an external information source to receive said input position data. The position controller may be configured and operable for accessing the input position data stored in a database of an inspection history.

In some embodiments, the system is configured for properly imaging the entire target having a certain depth (depth profile) larger than the depth of focus of the imaging unit. The position controller is configured and operable to determine a pitch distance, along the movement path, between consecutive plurality of images being acquired by the imaging unit, and control the motion and image acquisition of the imaging unit to capture the plurality of images such that each image is acquired at a different location along the depth profile of the target, thereby enabling generating focused images of the target along the whole depth of the target.

In some embodiments, the system includes at least one additional imaging unit configured for defining one or more measurement channels, for performing at least one of spectrophotometry, multi-spectral and UV-fluorescence measurements.

In some embodiments, the sensing unit comprises a plurality of distance sensing elements arranged in a spaced-apart relationship on a sensing surface having a predetermined geometry. Each of the distance sensing elements provides distance data indicative of a distance from the distance sensing element to the target location, the distance sensing data provided by the sensing unit being therefore indicative of a plane or volume map of the vicinity of the target location depending on the geometry of said sensing surface.

In some embodiments, the sensing unit comprises a one-dimensional array of distance sensing elements arranged transversely to the movement path of the optical probe and the imaging unit defines a two-dimensional array of imaging channels such that each distance sensing element is associated with a one-dimensional array of the imaging channels arranged in a spaced-apart relationship along the movement path of the optical probe.

In some embodiments, the system includes a distance controlling unit comprising a distance restriction assembly configured and operable to prevent the target from getting closer than a minimal focal distance of the imaging unit. The distance controlling unit may include at least one contact sensor configured and operable to detect at least a partial contact between the target and the distance restriction assembly and generate a contact signal indicative of the at least partial contact. For example, the distance controlling unit may include a plurality of such contact sensors associated with different parts of the distance restriction assembly, where each of the contact sensors detects at least a partial contact between the target and the respective part of the distance restriction assembly and generates a respective contact signal indicative of the at least partial contact. The control unit comprises a position controller configured and operable to be responsive to the contact signal(s) from the contact sensor(s) to initiate the imaging session(s) using one or more respective imaging channels of the imaging unit.

In some embodiments, the system includes a positioning assembly configured and operable to control the movement path of the optical probe in the vicinity of the target and adjust a position of the optical probe with respect to the target location, to enable one or more of the following: imaging underside, upper side or side of a plant part by the imaging unit, and reduce image smearing and blur during relative motion between the optical probe and the target. In some examples, the positioning assembly may include a rotatable telescopic member or a vertically extending telescopic pole carrying the optical probe. Alternatively or additionally, the positioning assembly comprises an orientation imaging sensor configured and operable to provide path data indicative of one or more obstacles or target parts located in the movement path of the optical probe. The control unit may be configured and operable to receive and analyze said path data, and selectively carry out at least one of the following: upon identifying the target parts in the path data, control the movement path of the optical probe in order to bring the target parts into the focal range of the imaging unit, and upon identifying one or more of the obstacles in the path data control the movement path of the optical probe in order to prevent collision of the optical probe with the obstacles. In some embodiments, the control unit is configured and operable to receive and analyze said path data by comparing the path data to previously collected data to enable selecting the target to be imaged.

In some embodiments, the positioning assembly is configured and operable to cause continuous or intermittent movement of the optical axis of the optical probe to compensate for a relative motion between the optical probe and the target. In some examples, the positioning assembly may be configured and operable to rotate the optical axis of the optical probe such that the optical axis scans around a conic surface, where a vector of the relative motion between the target and the optical probe is tangential to a base of the conic surface and is substantially equal to a vector of the movement of the optical axis when the optical axis points to the target. Alternatively, or additionally, the positioning assembly may be configured and operable to oscillate the optical axis of the optical probe along an oscillation path, where a vector of the relative motion between the target and the optical probe is tangential to at least a portion of the oscillation path and is substantially equal to a vector of the movement of the optical axis when the optical axis points to the target.

In some other examples, the positioning assembly is configured and operable to maintain said optical axis of the optical probe in a stationary position during the relative motion between the optical probe and the target, and, in response to data indicative of a condition that the target is entering an object plane of the imaging unit, controllably move the optical axis such that the relative motion between the target and the optical axis across the object plane is compensated and an image of the target is acquired.

In some embodiments, the system includes a plant shifting mechanism configured and operable to shift at least a part of the target with respect to the movement path of the optical probe. For example, the plant shifting mechanism is configured and operable to selectively carry out at least one of the following: shift said at least part of the target out of the movement path of the optical probe; and shift said at least part of the target towards the optical probe during movement and bring said plant part into the focal range of the imaging unit. The plant shifting mechanism may comprise parallel slides that are sloped at a leading edge of the optical probe and flattened at a distance from imaging channels of the imaging unit not exceeding a focal distance of the imaging unit.

In some embodiments, the imaging unit comprises a leaf imaging optical probe. For example, the leaf imaging optical probe may comprise a downward facing imaging element and an upward facing imaging element, whereby fields of view of the imaging elements essentially overlap, enabling imaging of both sides of a plant leaf without turning the plant leaf. In some other examples, the leaf imaging optical probe may comprise at least one flash illuminator element configured and operable to illuminate both sides of the plant leaf, and reflected light imaging is performed on one side of the leaf either simultaneously or sequentially with transmitted light imaging on the second side of the leaf.

The system may also include a chute configured to receive therein the plant leaf and enable said imaging of at least one side of the plant leaf by the leaf imaging optical probe.

The leaf imaging optical probe may comprise one or more of the following: a leaf holder assembly, a leaf guiding assembly, a leaf flattener assembly, and a leaf cutter assembly.

In some embodiments, the system comprises a purifier device configured and operable to decontaminate the optical probe. The purifier device may utilize one or more of the following to decontaminate the optical probe: heat, electrostatic electricity, vibration and or immersion in a purifying compound.

In some embodiments, the imaging unit is configured to capture a plurality of images of the target, each of the images with a different focal condition γ The inspection system further comprises an image analyzer configured and operable to detect in-focus portions in each of the plurality of images and merge the in-focus portions into a single in-focus image of the target.

In some embodiments, the imaging unit is configured to acquire a plurality of images of the target, each of the images being acquired with different imaging conditions including at least one of an illumination intensity and illumination angle. The inspection system further comprises an image analyzer configured and operable to detect optimally-illuminated portions in the plurality of images and merge the optimally illuminated portions into a single image of the target.

In some embodiments, the inspection system is configured as a hand-held device. The hand-held device may be of one of the following configurations: (i) the hand-held device comprises a common housing carrying said optical probe and said control unit; and (ii) the hand-held device is configured as a two-part unit carrying the optical probe and the control unit in respective first and second unit parts configured to be connected to one another.

In some embodiments, the inspection system is configured to be carried by a drone. The drone may comprise a plurality of rotors. The imaging unit may be mounted on an underside of the drone between the rotors. The inspection system may further comprise a wind blocking strip mounted between the rotors and a frame mounted inside the focal range of the imaging unit and below the wind blocking strip, with an offset along a movement direction of the drone. The drone can thus approach a plant leaf such that during the drone movement the leaf is brought between the wind blocking strip and the frame while the wind blocking strip affects a Bernoulli effect on the leaf keeping it floating until a point where a downdraft force of the rotors pushes the leaf downwards towards the frame and the at least one imaging unit acquires focused images of the plant leaf.

The invention also provides a vehicle carrying the above-described inspection system. This may be a ground vehicle or as a flying platform.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1 illustrates a non-limiting example of an inspection system configured in accordance with the principles of the present invention;

FIGS. 2A-2F illustrate non-limiting examples of the optical probe of the inspection system, in accordance with various applications of the present invention;

FIGS. 3A-3I illustrate non-limiting examples of positioning assembly of the inspection system and/or optical probe with respect to the target plant; and FIGS. 4A-4D3 illustrate non-limiting examples of a leaf imaging optical probe of the inspection system, in accordance with various applications of the present invention.

DETAILED DESCRIPTION OF EMBODIMENTS

Figure 2A:
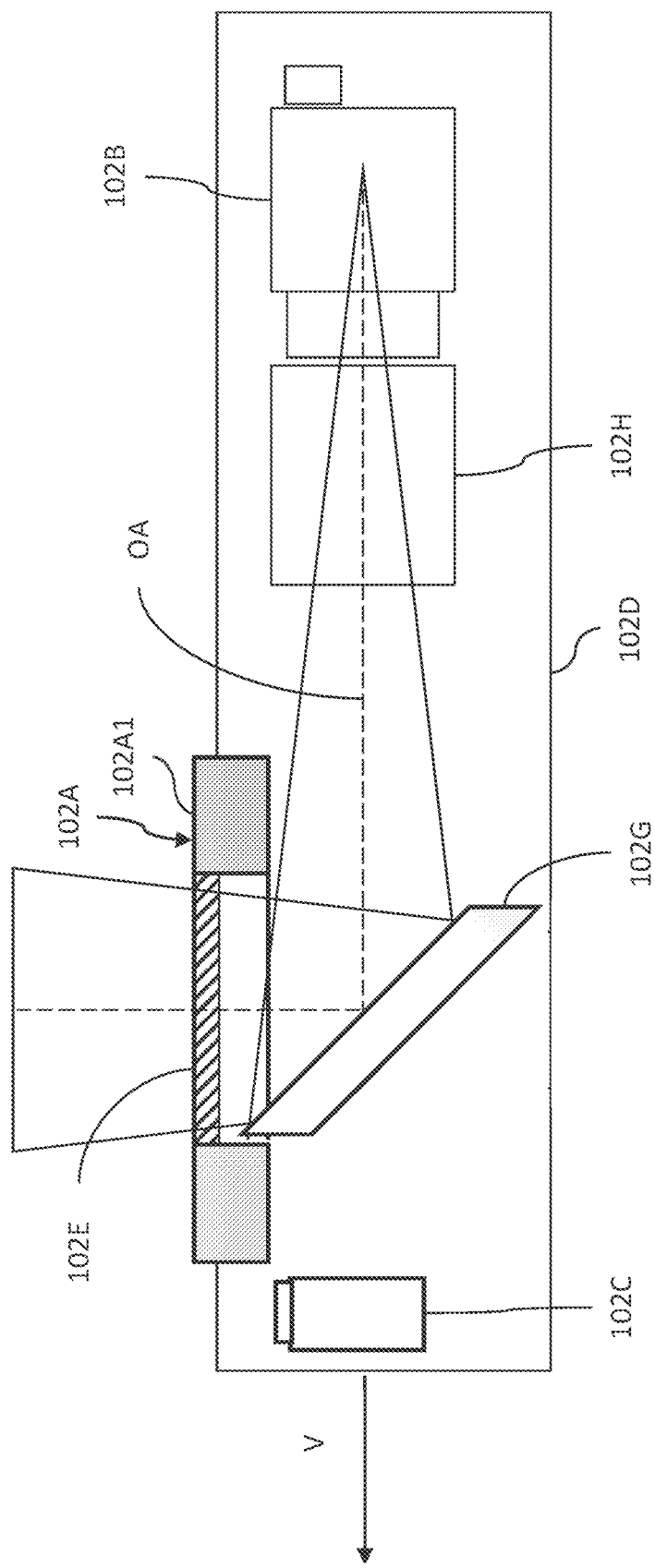

Reference is made to FIG. 1 illustrating by way of a block diagram a non-limiting exemplary embodiment of an inspection system 100 configured and operable for monitoring plants' conditions in one or more plant growth areas. For example, as shown, the inspection system 100 is configured to monitor one or more conditions of a plant 10, and more specifically a leaf 10L on the plant 10. The inspection system 100 includes an optical probe 102 configured and operable for collecting high-resolution characterization data from the plant 10 and a control unit 104 connected to the optical probe 102 by known in the art communication means 106, either wired or wireless communication, to exchange data therebetween. While not shown, the optical probe and the control unit can be equipped with suitable communication utilities, as known in the art, for enabling the data communication. It should be noted, however, that in some embodiments, the control unit 104 may be an integral part of the optical probe 102, and in this case the communication is done internally.

The optical probe 102 is configured to be brought close to the target and includes at least one flash illuminator unit 102A, at least one imaging unit 102B, and at least one sensing unit 102C, to perform one or more imaging sessions on the target, i.e. plant 10, at the target location, during a movement of the optical probe in the vicinity of the plant location, as illustrated by the movement/velocity vector V that points in the direction of the path of movement of the optical probe.

The sensing unit 102C includes a distance sensing element (in this non-limiting example, the sensing unit 102C is the distance sensing element), configured and operable to provide data enabling to determine an instantaneous distance D1 between the imaging unit 102B and the target location at plant 10, presented by a point/portion of interest POI at a leaf 10L of the plant 10, and generate distance sensing data DSD indicative thereof. In the described example, the sensing unit 102C measures the instantaneous distance D3 between the sensing unit 102C and the target POI where D3 is indicative of the distance D1 between the imaging unit 102B and the target POI, and more specifically D1 is indicative of the distance between the focal distance/plane of the imaging unit 102B and the target POI. The distance D1 can be obtained from the distance D3 based on previously known relation between them. The distance sensing element may be an optical sensor, an acoustic sensor, or other type of distance determining sensor.

The control unit 104 is configured and operable to be responsive to the distance sensing data DSD, via the communication means 106, to synchronize operation of the flash illuminator unit 102A and the imaging unit 102B to successfully perform the imaging sessions by the optical probe 102. The control unit 104 is a computer-based system and as such is configured with an input utility 104A and output utility 104B for receiving and sending data. Also, the control unit 104 includes a data processing and analyzing utility 104C that continuously analyzes the instantaneously received distance sensing data DSD and generates corresponding one or more signals to controllably activate the flash illuminator unit 102A and the imaging unit 102B. As shown in the figure, a distance D2 between the sensing unit 102C and the imaging unit 102B along the path of movement of the optical probe can be predetermined/known and used by the control unit 104 to determine the time at which the imaging session should be initiated or carried out, to thereby timely activate the flash illuminator unit 102A and the imaging unit 102B, with the respective imaging parameters, e.g. illumination intensity, illumination angle and illumination duration/time pattern of the flash light produced by the flash illuminator unit 102A, and time of image capture by the imaging unit 102B. By having access to the velocity of movement along the movement path, the control unit 104 can calculate the time passing between the moment at which the sensing unit 102C detects the target POI and the moment at which the flash illuminator unit 102A and/or the imaging unit 102B reach the target POI. In some embodiments, the target POI presents the edge of the target, e.g. the edge of a leaf, i.e. it is the first encounter between the sensing unit 102C and the target to be imaged. In this case, the initiation time of the imaging session is determined and the flash illuminator unit 102A and the imaging unit 102B are operated to start the imaging sessions which can last and extend over the whole target/leaf.

The imaging unit 102B defines one or more imaging channels each configured to provide high-resolution imaging. In this example, one imaging channel ICH is illustrated. The high-resolution imaging channel(s) capture(s) images of parts of plants, mainly flowers, leaves, fruit and branches, with the aim of detecting small elements such as pests, diseases and beneficial insects. Each high-resolution imaging channel has an optical resolution capable of imaging small elements to enable accurate recognition and classification. For example, the optical resolution is in the range of one micron to one hundred microns. For example, the field of view can be in the range of multiple millimeters to multiple centimeters. The high-resolution imaging unit 102B can enable detection, classification and mapping of the presence of detrimental conditions, e.g. detection and classification of the type of pests and its development phase (e.g. egg, larvae, adult), while also enabling, among others, analysis of the local ratio of beneficial insects to pest insects.

In some embodiments, in order to enable capture of high-resolution images without potential smearing effects caused by motion, either very short exposure times are performed, or the target and imaging channel are maintained with small differential motion during the image capture.

In order to detect many types of pests and diseases, the optical probe 102 can be configured to perform imaging of the underside of leaves, as that is the preferred habitat of many such pests, especially at the early stages of the pest development. The underside of leaves is less accessible to imaging from a stand-off position, since plants grow with leaf upper side facing outwards and upwards towards solar illumination.

Plant parts that are imaged in high-resolution, such as flowers, leaves, fruit and branches are essentially non-planar objects. Also, the underside of leaves of many types of plants is not a flat plane at the millimeter scale, potentially resulting in pests being partially hidden along protruding veins or along varying distances of different parts of the leaf from a flat focal plane. Therefore, in some exemplary embodiments, the imaging unit 102B is configured and operable to acquire a plurality of images with different focal conditions within a focal range of the imaging unit during the imaging sessions.

For example, the imaging unit 102B can be configured with a plurality of different imaging channels of the same optical resolution and different focal conditions, the distance sensing data DSD in this case may be indicative of the distance between each of the plurality of imaging channels and the target to be imaged. Additionally or alternatively, the imaging unit 102B may define at least one imaging channel that is configured with an adaptive/variable focus, within the focal range of the imaging unit, for imaging along the at least one imaging channel, the distance sensing data DSD in this case may be indicative of the distance between each of the at least one focus-variable imaging channel and the target to be imaged.

In some embodiments, the optical probe 102 can be accommodated within a housing 102D containing the flash illuminator unit 102A, the imaging unit 102B, and the sensing unit 102C. The housing may further include a portion thereof formed with at least one optical window 102E aligned with a respective at least one imaging channel ICH defined by the imaging unit 102B, to enable imaging of the target via the at least one optical window. At least part of the flash illuminator unit 102A can be accommodated within a peripheral region of the optical window 102E. For example, the optical window can have a circular shape while the at least part of the flash illuminator unit can have a ring shape surrounding the optical window.

In some embodiments, the housing 102D contains, instead of or in addition to an optical window, a portion thereof formed with at least one mesh screen (not specifically shown) aligned with a respective at least one imaging channel defined by the imaging unit 102B to enable imaging of the target via said at least one mesh screen. In one example, the mesh screen essentially includes an array of parallel lines/wires arranged parallel to a desired direction of the path of movement of the optical probe 102.

In some embodiments, the housing 102D includes a portion thereof, specifically a portion located upstream the sensing unit 102C (with respect to target location or path of movement of the optical probe), configured and operable as an aligner portion 102F that comes into contact with the plant part to be imaged such that it causes the plant part to align with respect to the flash illuminator unit and/or the imaging unit during the imaging sessions. For example, the aligner portion may act on the plant part to flatten it.

In some embodiments, the control unit 104 may include an image controller 104D configured and operable to controllably operate the imaging unit 102B to successively perform the imaging sessions, possibly with the different focal conditions. In some embodiments, the image controller 104D is configured and operable to determine the focal condition based on the distance D2 being indicative of the distance between the imaging system unit and the target. The distance D2 may form part of the distance sensing data DSD. The image controller 104D can be configured to determine the time sequence of operation of the flash illuminator unit and of the different imaging channels based either on their focus conditions, on the movement of the optical probe or on the distance sensing data DSD that is indicative of the distance between each of the imaging channels and the target. The image controller 104D can be configured to spatially divide the target into one or more sections and allocate one or more imaging channels for imaging each section, the plurality of images thereby covering the whole target. The image controller 104D may define the one or more sections such that fields of view of the one or more imaging channels in each section overlap. The image controller 104D may define the one or more sections such that fields of view of the one or more imaging channels are shifted along path of movement of the optical probe, for example the imaging channels are configured to capture images of respective sections arranged one after the other along the path of movement of the optical probe.

During image capture, the target may be illuminated by a flash or strobe light with short illumination time to prevent image smearing due to the movement of the optical probe with respect to the target. The flash illuminator unit 102A may include a single light source/lighting element, or multiple lighting elements, associated with each imaging channel ICH. For example, a ring of light sources surrounding the focus area can be provided. Each of the one or more lighting elements, associated with each imaging channel, can be aligned at a different angle with respect to optical axis of the imaging channel, and the control unit 104 can be configured and operable to determine the angle between the target location and the optical axis of the imaging channel, and select, for each imaging session, one or more of the one or more lighting elements to provide uniform illumination of the target. Multiple exposures may be performed at a frequency that can be adjusted to match the movement velocity of the optical probe and the size of the target. Pests or other elements of interest within the images can be captured in multiple images, thereby providing multi-angle data and enabling formation of a three-dimensional model of the object of interest. This can potentially aid in recognition and classification of the object of interest. The data from multiple images may be combined to form a two-dimensional image or three-dimensional model of the target.

The flash illuminator unit 102A can include multiple addressable lighting elements assigned to the different portions of the focal area and aligned to provide separate preferable illumination for each of the portions. The illumination may provide white light, red light or other spectral as well as various spatial options such as on-axis or oblique axis illumination. In some embodiments, a red low spatial frequency blocking filter can be added at a Fourier plane of the object in order to block green light received from the object and thereby reduce the intensity of essentially featureless green areas of the plants.

In some embodiments, the control unit 104 further includes a flash controller 104E configured and operable to control at least one of illumination intensity, illumination angle and illumination time pattern of the flash illuminator unit 102A. The flash controller 104E may control the at least one of illumination intensity, illumination angle and illumination time pattern of the flash illuminator unit based on input motion data indicative of the path of movement of the optical probe in the vicinity of the target location. The flash controller 104E can be also configured and operable to determine the illumination intensity, illumination angle and illumination time pattern based on one or more of the following: number of lighting elements of the flash illuminator unit, distance of focus plane, exposure time, ambient light, angle between the target and flash illuminator unit 102A, reflectivity of target, type of target plant, and type of part of the target plant. The inspection system may further include a movement detection unit 107 configured and operable for providing input motion data to the control unit 104, image controller 104D, flash controller 104E and/or position controller (described below), for controlling the imaging sessions and time sequence of operation of the flash illuminator unit and of the different imaging channels, including at least one of illumination intensity, illumination angle and illumination time pattern of the flash illuminator unit 102A. For example, as shown in the figure, the movement detection unit 107 can be integrated in the optical probe 102. The movement detection unit 107 can form part of the sensing unit 102C, for example at least part of the sensing unit provides the input motion data indicative of the path of movement of the optical probe in space. The movement detection unit may also be located in the control unit or on a vehicle carrying the optical probe and/or the control unit. In some embodiments, the input motion data includes one or more of position, velocity vector and/or acceleration vector.

In some embodiments, the optical probe 102 includes a plurality of sets, each set includes a flash illuminator unit, a respective imaging unit and a respective sensing unit and each set is oriented in a different spatial and/or angular direction with respect to an axis of the optical probe. This enables capturing images from multiple directions, thus facilitating the data collection and the reconstruction of the three-dimensional model of the plant part under examination. Each set may be associated with respective image controller and flash controller configured and operable as described above. In one example, a first set of a flash illuminator unit, a respective imaging unit and a respective sensing unit faces upwards, a second set faces downwards, and a third set faces horizontally.

In some embodiments, the inspection system includes an indication unit 108 configured and operable to provide indication about an operational state of the optical probe. The operational state can be, for example: on/off, waiting for target identification, target has been identified, capturing images of target, failure message(s), etc. The indication unit 108 may utilize audio, visual and/or vibration signals to indicate the specific operational state of the probe. The indication unit 108 can be particularly useful when the optical probe is manually carried and operated by a worker in the field.

In some embodiments, the inspection system further includes, as part of the imaging unit 102B or as a standalone device, an imaging device configured and operable for defining one or more measurement channels, for performing at least one of spectrophotometry, multi-spectral and UV-fluorescence measurements, for characterizing the target plant.

In some embodiments, the sensing unit 102C includes a plurality of distance sensing elements arranged in a spaced-apart relationship on a sensing surface having a predetermined geometry, each of the distance sensing elements providing distance data indicative of a distance from the distance sensing element to the target location, the distance sensing data provided by the sensing unit being therefore indicative of a plane or volume map of the vicinity of the target location depending on the geometry of the sensing surface. For example, the sensing surface may trace a cylindrical surface, a spherical surface, a flat surface, etc.

In some embodiments, the sensing unit 102C includes a one-dimensional array of distance sensing elements arranged transversely to path of the movement of the optical probe and the imaging unit defines a two-dimensional array of imaging channels such that each distance element is associated with a one-dimensional array of the imaging channels arranged parallel to the path of movement of the optical probe.

In some embodiments, the imaging unit 102B includes multiple imaging sensors with respective separate focusing mechanisms. The sensing unit 102C may include multiple distance sensing elements for measuring distances to different areas of at least one target. The flash illuminator unit 102A may include multiple lighting elements for illumination of the at least one target. In some examples, the multiple imaging sensors and/or distance sensing elements and/or lighting elements are located in a two-dimensional plane, arranged in a line, in a circle or in other patterns within the plane. The multiple imaging sensors and/or distance sensing elements and/or lighting elements may also be located on a three-dimensional surface such as a cylinder or a rectangular box. The multiple distance sensing elements may be arranged in a pattern on the surface to enable building a three-dimensional distance map of the at least one target.

Multiple imaging sensors may be located in a linear arrangement parallel to the path of movement of the optical probe. In one embodiment, the imaging sensors are triggered sequentially, with a time delay depending on the forward movement velocity, such that each of the imaging sensors captures an image of essentially the same part of the plant. The time delay is essentially equal to the distance between the cameras divided by the velocity of the movement. Separate illumination flashes can be operated for each imaging sensor. The separate imaging sensors may operate with different focal distances, to build a three-dimensional image of the plant part by focus stacking, as will be described further below. The separate imaging sensors may also operate with different illumination intensity levels to enable capturing of images with optimal exposure levels or for combining images of objects with different levels of reflectivity into a composite image with optimal exposure level. The exposure levels may be adjusted to compensate for changes in target distance, target angle, target reflectivity, ambient illumination and others. The intensity levels may also be adjusted in conjunction with the different focal distance of each imaging sensor.

In some embodiments, the distance between the imaging sensors is less than the width of the field of view of the imaging sensors at the target plane, enabling overlap of the fields of view of the imaging sensors. When the delay between imaging operation of sequential imaging sensors is less than the inter-sensor spacing divided by the velocity, the different imaging sensors may provide images of essentially the same object from different angles enabling formation of stereoscopic images for extraction of three-dimensional information.

In some embodiments, at least two imaging sensors may be adjusted so that their optical axes are not parallel, but essentially pointing to the same location at the nominal target plane. At least two images may be captured simultaneously to enable formation of detailed stereoscopic images for extraction of three-dimensional information.

Multiple images from multiple directions may be used to produce a continuous image of the circumference of a semi-cylindrical target such as a leaf's vein in order to detect and recognize pests that hide in recesses along the veins.

When at least one target enters the range of the distance sensing element(s), the control unit 104, specifically the data processing and analyzing utility 104C, processes the distance signals DSD and builds a three-dimensional model of the location of the target. If the at least one target is not located in sufficient proximity to the imaging sensor(s), the control unit 104 may generate a signal, requesting to correct the location of the imaging unit with respect to the target in order to optimize distance for the capturing of images of the at least one target. Based on the distance information, the control unit defines the focus distance setting for each of the imaging sensors of the imaging unit in order to capture focused images of the different areas of the at least one target. The control unit also defines the specific lighting elements to be operated in order to provide uniform illumination for the imaging sensors to be operated. Images may be captured simultaneously during a simultaneous light pulse, or sequentially with separate pulses.

As will be described further below, the inspection system may process the images or may send the images to an external image analysis utility to process the images. Processing of the images may include combining in-focus areas of each of the images from the multiple imaging sensors/channels into one image containing an extended in-focus area. The in-focus area for each imaging sensor/channel may be determined by combining the nominal camera focus range (e.g. depth of focus, depth of field or other definition) with the data from the three-dimensional distance map and finding the in-focus areas of the three-dimensional surface. The inspection system may vary the parameter for determining the focus range in order to decrease or increase the overlap of information from the different imaging sensors/channels on the three-dimensional surface. Based on the known focus setting of each imaging sensor/channel, the inspection system may perform magnification normalization and distortion correction of the images prior to combining them. The inspection system may analyze the separate images and detect in-focus areas in the separate images and combine them into a single image containing the multiple in-focus areas. The inspection system may detect localized in-focus elements of interest in the separate images and combine them into an image containing multiple localized in-focus elements.

The inspection system, e.g. the control unit, may define which imaging sensor(s) or unit(s) will be used in order to minimize data file size if it detects that certain areas will have over-redundancy of multiple images or if certain areas will not contain a target in focus. The inspection system may delete images after image capture as well, based on the results, e.g. if there are no in-focus areas in the images. The inspection system may operate all the imaging sensors and/or lighting elements or a subset thereof depending on the three-dimensional shape of the target. Depending on the geometry of the surface containing the distance sensing elements, the three-dimensional map may be formed above a plane containing the distance sensing elements, if the distance sensing elements are located on a plane, or if the distance sensing elements are located on a cylindrical surface, the three-dimensional map may be formed in the cylindrical volume surrounding the cylindrical surface.

The location of the sensing unit(s), flash illuminator unit(s) and imaging unit(s) on the housing of the optical probe may be determined by the type of plant to be inspected. Different types of plants may have different typical angles of their leaves depending on plant species, plant age, plant hydration and other factors. Angle of the imaging channel(s) with respect to the target may be varied in order to enable essentially perpendicular imaging and increase the proportion of in-focus areas of the captured images. The angle may be controlled by providing a rotating portion of the optical probe that adjusts the angle during operation, or may be preset in manufacturing of the optical probe making the optical probe specific to a specific kind of crop.

The optical probe may be surrounded, at least at the vicinity of the optical window, by a mesh casing or screen that prevents direct contact of parts of the target plant with the functional parts of the imaging (the flash illuminator unit and the imaging unit). The mesh casing/screen may be designed with high opening/blocking ratio to minimize the blocking of the images. The distance of the mesh from the imaging unit is designed to prevent the plant parts from getting closer than a minimal focal distance.

The mesh surrounding the optical probe may contain at least one contact sensor (as will be further described below) which detects when a part of a plant comes into contact with the mesh. The signal generated by the sensors may be processed and used to trigger illumination and image capture. Sensors in specific parts of the mesh may be used to trigger specific imaging sensors of the inspection system.

Figure 2B:
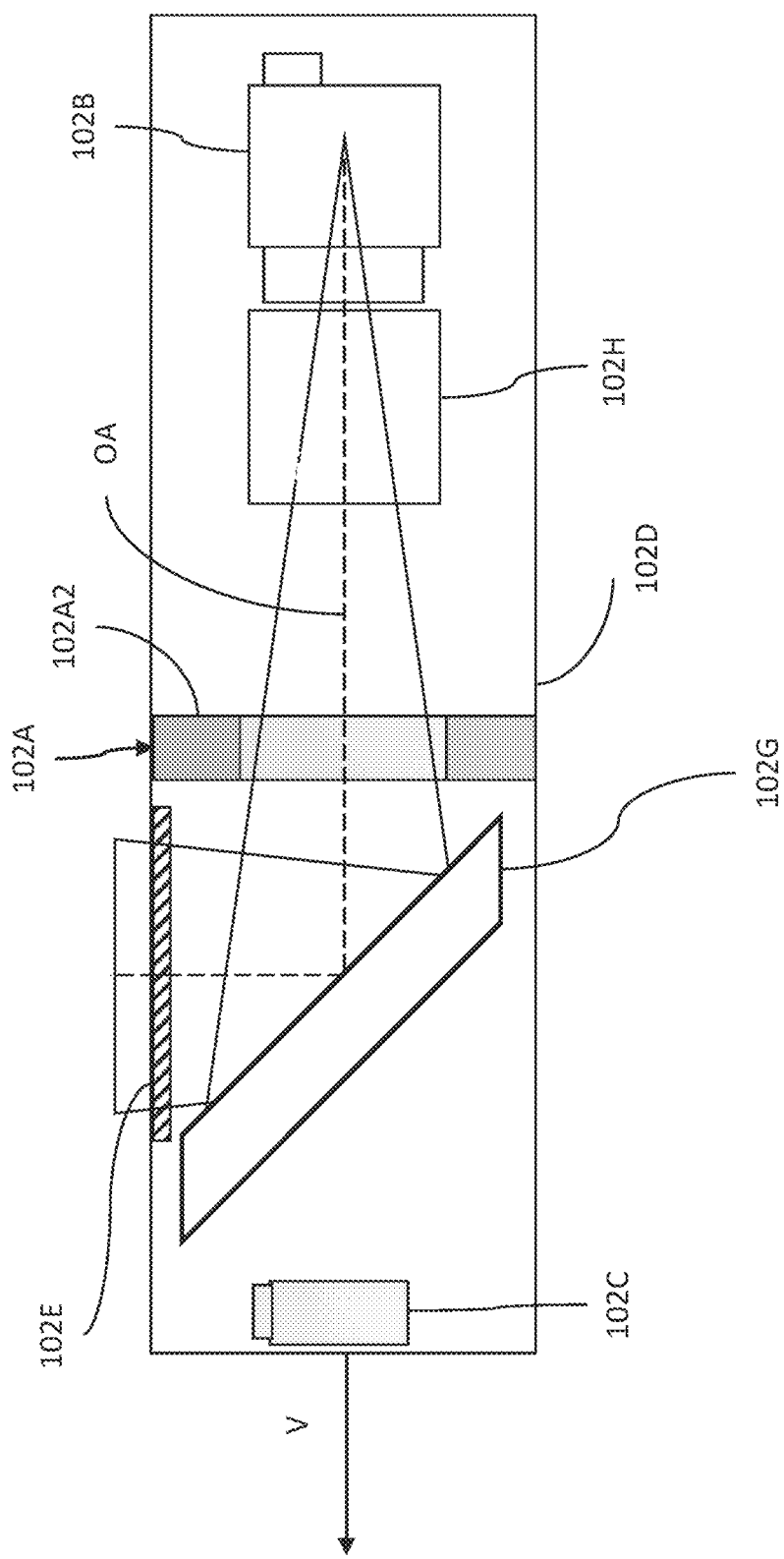

Reference is made to FIGS. 2A-2F illustrating non-limiting examples of different configurations of the optical probe 102, in accordance with the present invention. Different physical and/or optical designs of the optical probe can be considered. For example, the imaging channel ICH starting at the target, passing through an optical window in the housing and ending at a detector of the imaging unit may not be straight, i.e. may not be on-axis imaging channel, as illustrated generally in FIG. 1, but a broken optical path, i.e. a folded axis imaging channel, as illustrated in FIGS. 2A and 2B. This can be due to physical constrains such as size of the imaging unit used against the optimal size of the housing of the optical probe to provide effective positioning and access of the optical probe to the different plant parts. Sometimes, it is preferable to minimize the height of the housing of the optical probe as much as possible, resulting, for example, in placing the imaging unit in an off-axis position with respect to the optical window, as in FIGS. 2A and 2B. Sometimes, it is preferable to minimize the length of the housing of the optical probe as much as possible, resulting, for example, in placing the imaging unit beneath the optical window, as in FIG. 1.

When the imaging unit is placed off-axis with respect to the optical window, as in FIGS. 2A and 2B, the optical probe further includes at least one light directing/reflecting element 102G, such as a mirror, that directs the light along the imaging channel. Also, as illustrated in the figures, the optical probe may include a light focusing element 102H, such as a lens, placed before the imaging unit, in particular between the at least one directing element 102G and the imaging unit 102B. The folded-axis configurations enable, among others, small mechanical cross-section with relation to the direction of motion while still enabling full field of view. The sensing unit 102C may be placed at different locations in relation to the optical axis (upstream of the light directing element 102G with respect to a direction of propagation of the input light) with a detection axis parallel to the optical axis, enabling positioning the imaging channel ICH downstream of the direction of path of movement (direction V as shown), upstream of the direction of path of movement or at different angles in between.

As illustrated in FIG. 2A, at least one lighting element 102A1 of the flash illuminator unit 102A associated with the respective at least one imaging channel is positioned upstream of the light directing element 102G with respect to a direction of propagation of the input light. In this example, the at least one lighting element 102A1 is external with respect to the housing. The optical window 102E can be located adjacent to the illuminator unit 102A1, without any distance therebetween, enabling sealing of the housing. Also, this configuration has less parasitic scattered light originating from the lighting element 102A1, thus enhancing flash efficiency and image clarity while saving energy.

As illustrated in FIG. 2B, at least one lighting element 102A2 of the flash illuminator unit 102A associated with the respective at least one imaging channel is positioned downstream of the light directing element 102G with respect to a direction of propagation of the input light. In this example, the at least one lighting element 102A2 is internal with respect to the housing. The optical window 102E can be located between the target and the light directing element 102G, facilitating sealing of the housing with the window.

In FIG. 2C1, the optical probe 102 is accommodated in a two-part housing, such that the flash illuminator unit 102A and the imaging unit 102B are accommodated in a first housing part 102D1, and the sensing unit 102C and a light directing element 102G are accommodated in a second housing part 102D2. This configuration enables, among others, the possibility to rotate the second housing part 102D2 around the optical axis OA, thereby enabling rotation of the object plane and rotating the folded optical axis OA1 while maintaining the sensing unit 102C aligned to the object plane as illustrated in FIG. 2C2. This enables access to targets in different directions around the optical probe, as illustrated in three such directions (down, diagonally up, right), while using one flash illuminator unit and one imaging unit oriented in only one direction. In some embodiments, the position of sensing unit 102C and the rotation rate can also be adjusted to essentially cancel the relative motion of the target relative to the optical probe. Alternatively, when the optical probe is located within a single housing, the whole housing can be mounted on a rotatable joint/pivot that rotates the housing and enables capturing images of plant parts located in different directions relative to the optical probe.

As mentioned above, the optical probe may contain at least one reflective optical element, which is located within the field of view of the imaging unit, at an axial distance close to the object plane where the reflective element tilts the angle of the rays to cause the imaging unit to image an off-axis area instead of an on-axis or near-axis area. In some embodiments, two mirrors are placed within the field of view of the imaging unit, such that one causes an area above the optical axis to be imaged onto a first portion of the imaging sensor, and a second mirror causes an area below the optical axis to be imaged onto a second portion of the imaging sensor and a third unaffected area of the field of view is imaged onto a third portion of the imaging sensor. In a specific embodiment, the first mirror causes an essentially upward-facing perpendicular axis to be formed at an object plane and the second mirror causes a downward-facing perpendicular axis at a second object plane to be formed, and the imaging sensor contains separate image areas formed from the first object plane, the second object plane and portion of the non-deflected original object plane. In an additional embodiment, the mirrors may be rotated around the optical axis to enable image capture of various targets off the optical axis. In an example, the different areas of the plant may be the underside of a first leaf, the top side of a second leaf and the stem of the plant. The position of the optical axis may be maintained at a height essentially half way between the upward facing top side of a leaf and the downward facing underside of a leaf, while pointing at a stem of the plant in the non-deflected direction. The distance sensing element(s) of the sensing unit may be used to measure the distance to the objects of interest and bring the optical system to a position essentially equidistant to multiple objects of interest. Alternatively, the system may determine a motion path where the different parts of the plant are brought to focus sequentially.

Figure 2D:
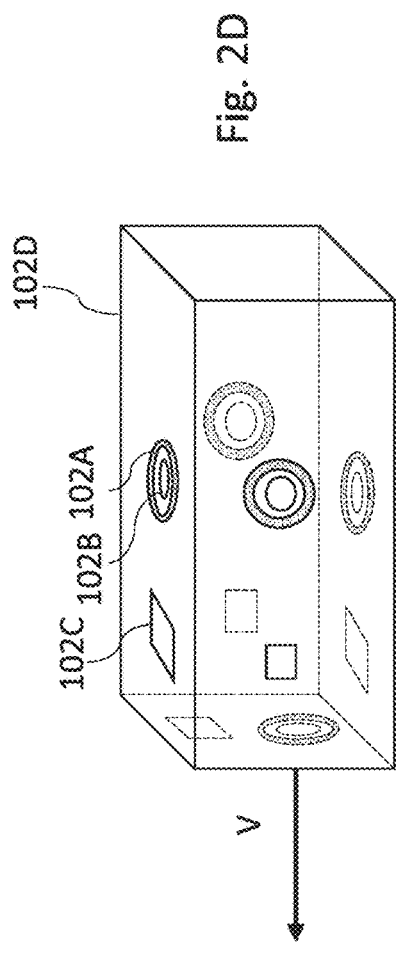

FIG. 2D illustrates a non-limiting example of an optical probe 102 accommodated in a housing 102D having a rectangular box shape, with four or five sets of flash illuminator unit 102A having a ring shape, imaging unit 102B and distance sensing unit 102C, mounted on each one of the rectangular surfaces of the box and defining four or five sensing surfaces. This enables high flexibility for capturing images of the plants without the need to turn and move the optical probe frequently. The direction of motion (motion axis) V is defined to enable simultaneous capturing of images in the forward, upward, downward and sideways directions. The optical probe may also be inserted in a plant while generating distance data, then held in place and operated statically. A similar example may be implemented on a cylindrical box, with the cylinder axis perpendicular to the direction of motion.

Figure 2E:
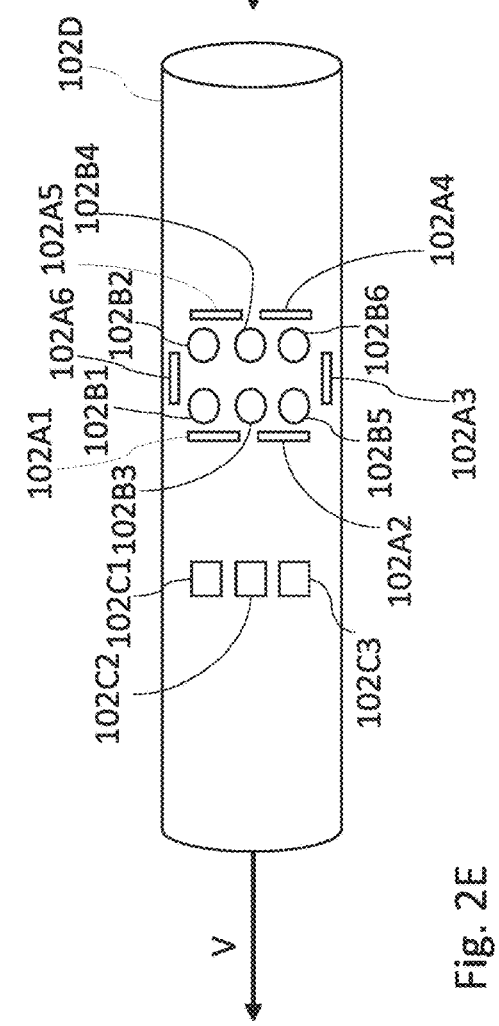

FIG. 2E illustrates another non-limiting example of an optical probe 102 accommodated in a housing 102D having a cylindrical shape, with one set of flash illuminator unit 102A, imaging unit 102B and distance sensing unit 102C, mounted on the surface of the cylinder and defining a sensing surface. The distance unit includes a plurality of distance sensing elements, e.g. 102C1-102C3, arranged in a one dimensional array along a transverse direction to the motion axis of the optical probe, the imaging unit includes a plurality of imaging sensors, e.g. 102B1-102B6, arranged in a two-dimensional array along the longitudinal and transverse directions, such that two imaging sensors are associated with each distance sensing element located along the same line along the longitudinal axis, the flash illuminator unit includes a plurality of lighting elements 102A1-102A6 associated with and surrounding the imaging unit.

Figure 2F:
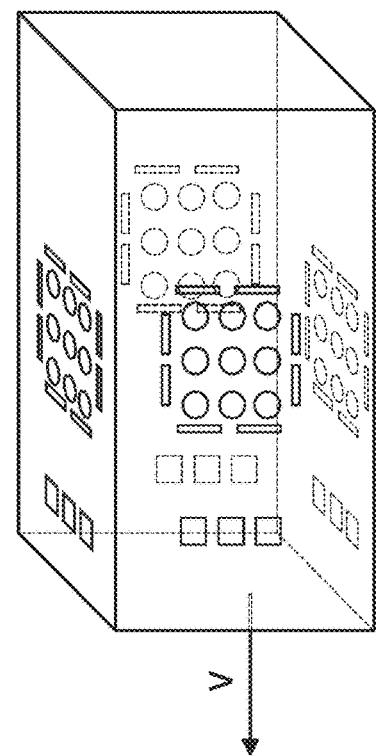

FIG. 2F illustrates another non-limiting example of an optical probe 102 accommodated in a housing 102D having a box-like shape, with a set of flash illuminator unit 102A, imaging unit 102B and distance sensing unit 102C, mounted on multiple surfaces of the box and defining multiple sensing surfaces. The distance unit includes a plurality of distance sensing elements, e.g. three, arranged in a one dimensional array along a transverse direction to the motion axis of the optical probe, the imaging unit includes a plurality of imaging sensors, e.g. nine, arranged in a two-dimensional array along the longitudinal and transverse directions, such that three imaging sensors are associated with each distance sensing element located along the same line along the longitudinal axis, the flash illuminator unit includes a plurality of lighting elements, e.g. six, associated with and surrounding the imaging unit.

As appreciated, various options of sets and arrangements are possible enabling flexibility, efficiency and time management.

Reference is made to FIGS. 3A-3I illustrating non-limiting examples of positioning assemblies of the inspection system and/or optical probe with respect to the target plant. The positioning assembly(s) may be configured and operable to control path of the movement of the optical probe in a vicinity of the target and adjust a position of the optical probe with respect to the target location.

Figure 3A:
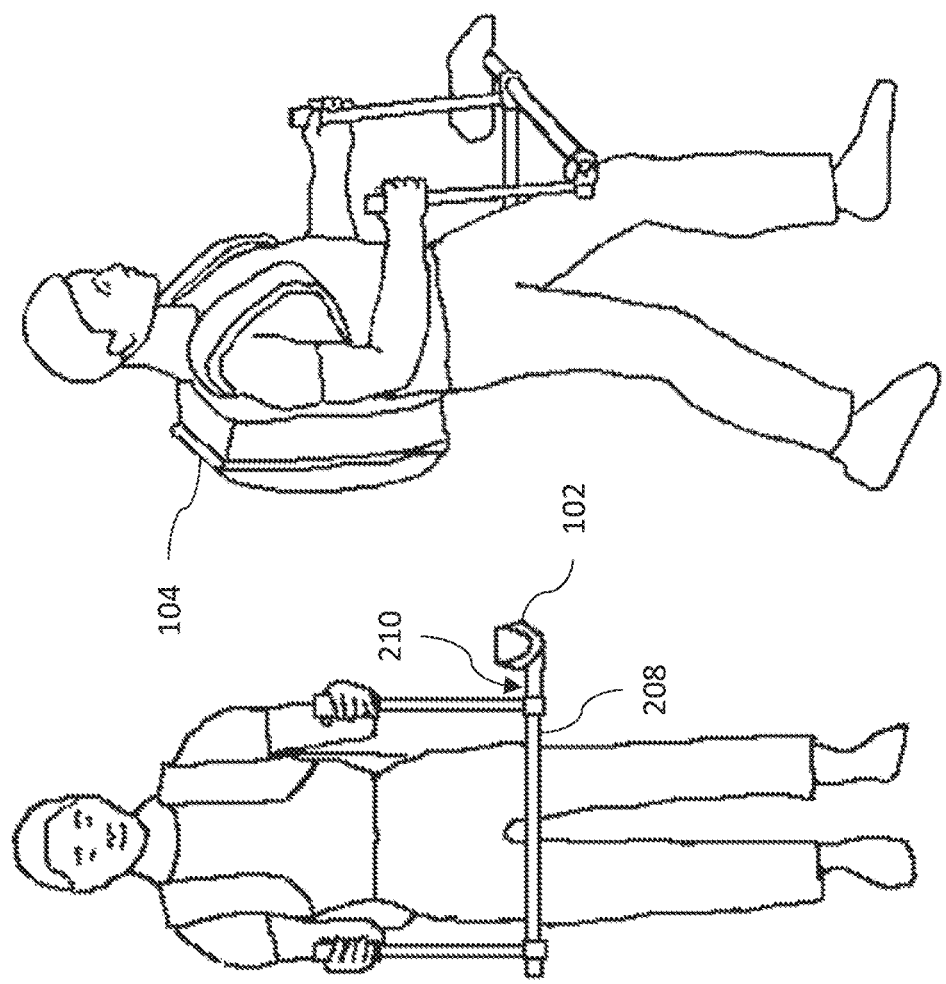

In some embodiments, as illustrated in FIG. 3A, the inspection system or at least the optical probe can be carried by a worker, the optical probe 102 is configured as a hand-held device which the worker manually holds and brings in proximity to the target plants in order to perform the imaging session(s). The control unit 104 can be carried by the worker, for example on his/her back as shown, or on the hand-held device.

Figure 3B:
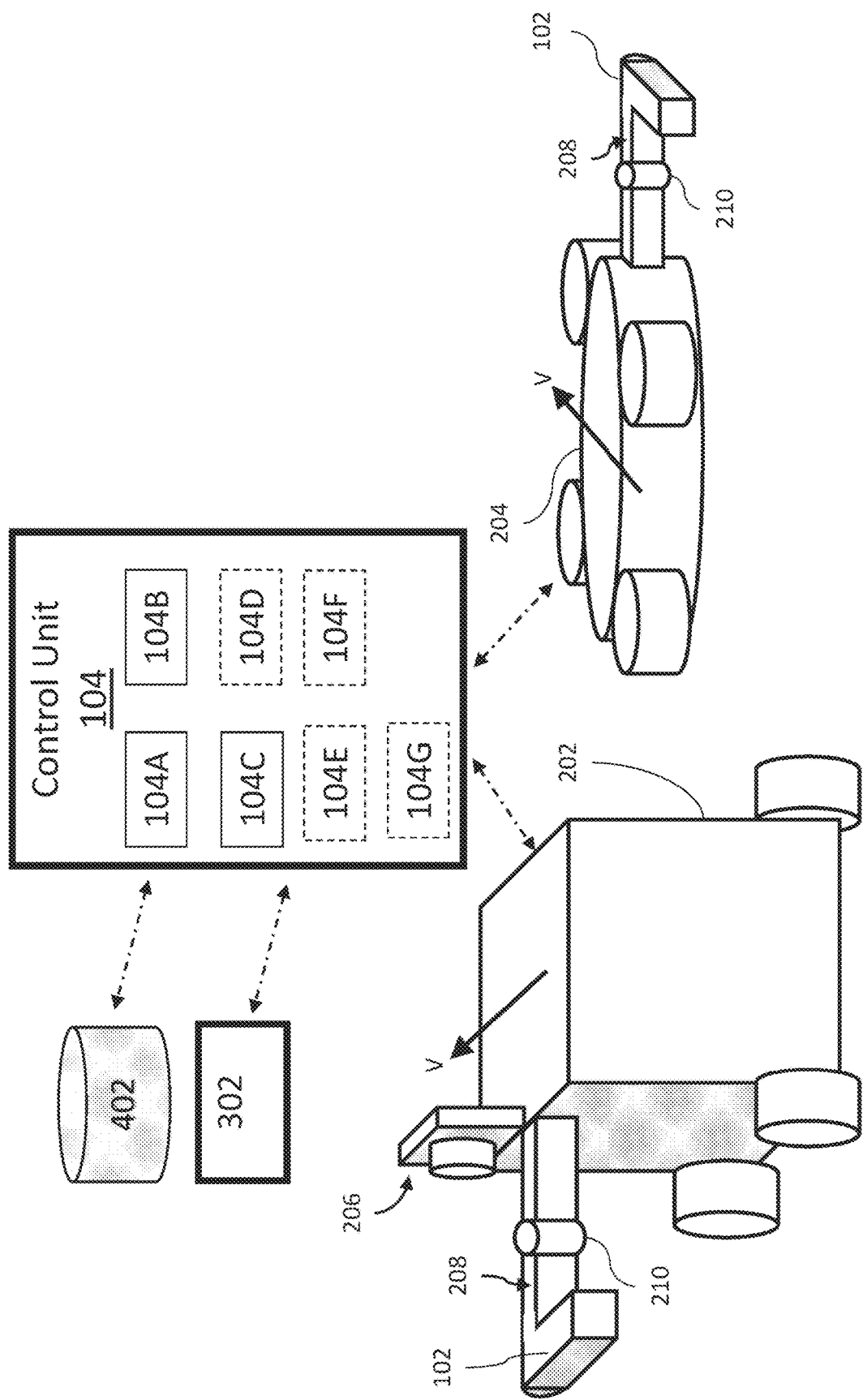

In some embodiments, as shown for example in FIG. 3B, the inspection system or at least the optical probe can be carried by a vehicle, specifically a robotic transportation vehicle, that travels in the area of crops, e.g. along rows of crops, and is brought into proximity to the plants in order to capture images of the target plant parts such as flowers, leaves, fruit or branches. As shown, the vehicle can be a ground vehicle 202 or a flying platform 204 (e.g. a drone).

The target locations to be inspected may be provided by an external information source 302 and/or may be chosen autonomously by the inspection system and/or may be predetermined based on previous inspection history, and/or may be predetermined based on a path designed to provide effective statistical sampling of the area.

The positioning assembly includes a position controller 104F that may be located in the control unit 104, as illustrated in the figure, or in the vehicle 202 or 204, or distributed therebetween. The position controller 104F is configured and operable to control a position of the optical probe with respect to the target location based on input position data. The position controller 104F can be configured and operable to communicate with the external information source 302 to receive the input position data. The position controller 104F can be configured and operable to receive input data of the movement detection unit 107 located in the optical probe, in the control unit or in the vehicle. Additionally or alternatively, the position controller 104F can be configured and operable for accessing the input position data that is stored in a database 402 of previous inspection history. The position controller 104F can be configured and operable to control spatial orientation and/or path of movement of the optical probe with respect to the target location, based on previously provided orientation data or based on input from an orientation imaging sensor 206, as further described below.

The external information source 302 can be configured to provide the input position data or the orientation data to the position controller 104F by analyzing previously captured images of the plants and determining candidate locations that are considered suspicious for possible presence of pest or disease. The images may be captured by a wide-area imaging channel that can be located on a separate vehicle or on the vehicle carrying the high-resolution channel. The analysis of the images is carried out by the position controller 104F or by an image analyzer 104G located in the control unit (as shown) or in the external information source or in both. In some embodiments, the image analyzer may be located on the vehicle carrying the high-resolution channel or the wide-area channel, or it may be located in a separate location, such as the control unit, while communicating with a controller on the vehicle carrying the high-resolution channel. The analysis of the wide-area images may define preferred targets and provide calculated access paths for accessing those targets. For example, it may provide approach vectors for the high-resolution channel to inspect the targets while providing for minimum physical interaction with the plant.

In one embodiment, a series of wide-area images covering most of the areas of a row of plants is analyzed by the position controller 104F/image analyzer 104G for suspicious locations on plants which show a possible presence of pests, disease or other detrimental conditions. Based on the analysis, the position controller 104F/image analyzer 104G provides a series of preferred target locations which may include flowers, leaves, fruits and branches of different plants along the row. The position controller 104F may also provide information on an approach path for accessing the preferred targets. Furthermore, the position controller 104F/image analyzer 104G may select certain targets located in close proximity to enable inspection with one approach path. The position controller 104F/image analyzer 104G may also provide an optimal sequence for inspecting the targets. If the time required for inspecting the suspicious targets is less than a predefined time, the position controller 104F/image analyzer 104G may add additional targets to optimize a uniform coverage of the plant area up to a predefined maximum time.

The target objects/plants may be defined in advance by the position controller 104F as part of an inspection path, where specific areas of the crop are defined for specific types of samples. For example, when inspecting a row of plants, the position controller 104F may define areas of the row where leaves are to be examined (in x, y, z coordinates), areas where fruit are to be examined, areas where flowers are to be examined and areas where branches are to be examined. Leaves may be examined on their top side, their bottom side or both. The procedure for automatically defining the areas to be examined may take into account the age of the plants, the height of the plants, previous history of findings on the plants, the season, the past weather history, the future weather forecast, the allotted time for inspecting the area of plants and other factors. The position controller 104F may select locations where in a single approach, multiple targets may be accessed, for example a location where the top side of a leaf, a branch and a bottom side of a leaf can all be viewed from a single access path. The position controller may also provide a general area to be examined, where the exact plant part to be inspected is determined when approaching the general area, based on input from the orientation imaging sensor 206.

Images captured during the approach to a target, by a wide-area imaging channel or by an orientation imaging sensor, may be stored in the database 402 and utilized later. If a disease or pest is found at the specified target, the wide-area images from the approach may be utilized for improving correlations between wide-area images of a plant and the locations in which diseases are present. The preferable images which may be utilized may include at least one of an image of the pest or disease, an image of the plant part containing the pest or disease, and an image of the plant including the vicinity of the plant part containing the pest or disease.

The target information transferred to the high-resolution inspection system may be in the form of x-y-z coordinates, in the form of at least one target reference image, in the form of a three-dimensional coordinate path, in the form of at least one target reference image and a three-dimensional path or any other format containing the required information.

As mentioned above, the positioning assembly may contain an orientation imaging sensor 206 with a wide-area field of view. The orientation imaging sensor 206 may be a conventional imaging camera or a stereoscopic or other three-dimensional camera providing information on distance as well as lateral location. The orientation imaging sensor 206 may be mounted on the same optical probe as the high-resolution imaging unit or at a location on the vehicle, preferably more distant from the row of plants to maintain a wider field of view, or at another vehicle or in fixed locations in the plant growth area. The orientation imaging sensor 206 may be configured and operable to provide image path data indicative of obstacle(s) or plant parts located in the path of movement of the optical probe. The control unit, specifically the position controller 104F, is configured and operable to receive the path data and upon identifying plant parts in the path data, control the path of movement of the optical probe in order to bring the plant parts into the focal range of the high-resolution imaging unit. Additionally or alternatively, the position controller is configured and operable to control the path of movement of the optical probe in order to prevent collision of the optical probe with obstacles upon identifying one or more obstacles in the path data. The position controller may also be configured and operable to receive and analyze the path data by comparing the path data to previously collected data to enable selecting the target to be imaged.

When the optical probe is in motion and passes above (or below) a target to be imaged, the input from a forward-facing orientation imaging sensor may be used to adjust the height of the optical probe in order to bring a bottom (or top) facing focus area to the height of the target.

When approaching a specified target location, images from the orientation imaging sensor may be compared to a target reference image received from the position controller and upon finding a high correlation between images, the target location is determined. As the vehicle approaches the plant, vertical height and lateral position adjustments are made based on images from the orientation imaging sensor in order to accurately engage specified target. In the case where the inspected targets are chosen autonomously by the inspection system/optical probe/position controller, the orientation imaging sensor may be used to determine the plant parts to be examined, such as flowers, fruit, leaves, branches, top side of leaves and underside of leaves. Wide area images of the plant captured by the orientation imaging sensor may be analyzed by the position controller or by a processor on-board the vehicle, and candidate plant parts are selected from the images based on, for example, accessibility, suspicious distortion, discoloration and other characteristics. The position controller may provide coordinates and directions to reach the desired location for inspection of the plant part. In one example, the vehicle carrying the optical probe travels along a row of plants and periodically stops at predetermined distances, captures a wide-area image of the plants, determines a target plant part and approach path, approaches the target on the path and performs inspection of the plant part. In another example, the vehicle carrying the optical probe travels continuously along a row of plants and the position of the high-resolution optical probe is continuously adjusted to enable imaging within the plant foliage. In one specific example, the position of the high-resolution optical probe is adjusted to enable the optical probe to pass underneath leaves, where the movement path of the probe in relation to the leaves is controlled in order to prevent entanglement and damage to the plant or probe.

The position adjustment enables bringing the probe to a focus position relative to the leaves, thereby enabling sampling of maximum number of leaves while maintaining essentially constant forward motion along the row. The vertical position of the focal area of the optical probe may be adjusted by varying the height of the vehicle, by varying the height of the interface between the vehicle and the optical probe or by varying an internal distance between optical elements in the optical probe.

In some embodiments, the high-resolution optical probe is mounted on a drone small enough to enter spaces between the leaves of the plant. The drone is preferably encased in a rounded net-like enclosure, through which air can flow, enabling efficient flight, while gaps in the net-like structure are small enough to prevent contact of the leaves with the drone's moving parts. At least one optical probe/imaging unit is located within the net-like enclosure and attached above the drone, with an optional gimbaled mounting. Attaching the optical probe above the drone provides easy access to imaging underside of leaves. The downdraft caused by the drone's propellers may pull a nearby leaf towards a meshed surface located at the focal plane of the at least one optical probe/imaging unit. The vertical distance between the mesh and the drone rotors is designed to enable the suction force of the downdraft to move and essentially flatten the leaf on the meshed surface, but not to result in strong adhesion of the leaf which could cause unwanted drag on the lateral motion of the drone. Once the leaf is contacted, the drone goes into hover mode and after the leaf is flattened, an image is captured by the optical channel. The leaf may then be released, for example the drone may momentarily reduce motor speed while performing a yaw rotation.

In some embodiments, the drone approaches a target leaf from below, and once contact is made and the leaf is brought to the focal plane of an upwards facing imaging channel, the drone goes into hover mode, after which an arm is rotated outside the mesh bringing a second imaging channel into a focus position on the upper surface of the leaf. Optionally, an additional arm is rotated, and a frame shaped clamp is placed onto the upper surface of the leaf prior to positioning of the second imaging channel.

As illustrated in FIGS. 3C1-3C2, attached to the underside of a drone 204 is at least one of a downward facing imaging unit 102B1 is and an upward facing imaging unit 102B2 where the distance between the upward and downward facing imaging units is equal to the sum of the focal lengths of the imaging units. A wind blocking strip 310 is attached below the drone in an area between rotors, resulting in a Bernoulli effect area. The blocking strip starts at the outer edge of the drone and ends slightly outward from the location of the imaging sensor(s). A frame 311 is located at the level/plane in which both imaging sensors' focal areas coincide. A part of the frame forms a horizontal support plane at the focal plane of the imaging sensor. A distance sensing element 102C is mounted near the end of the blocking strip to provide distance information from the leaf, and an outward facing orientation imaging sensor 206 provides lateral location data of the leaf with respect to the imaging unit to the position controller 104F. The drone flies near a target leaf 10L in a direction that brings the leaf under the blocking strip using information from the orientation imaging sensor 206 and the distance sensing element 102C. The Bernoulli effect keeps the leaf in a relatively high position until the tip of the leaf passes out of the range of the blocking strip, whereupon, the leaf is blown downwards by the downdraft of the rotors onto the frame at the imaging unit focal plane. The information provided by the distance sensing element 102C is used by the position controller 104F to maintain the correct height of the drone in relation to the leaf. The downward draft of the drone flattens the leaf onto the frame after which images are captured by one or both imaging sensors.

Figure 3D:
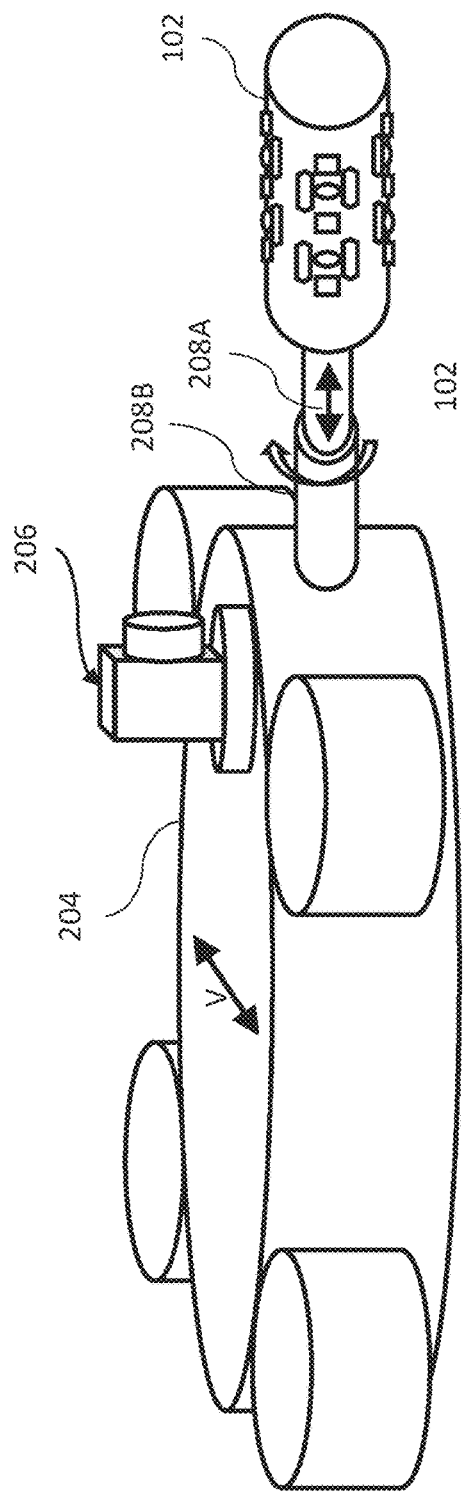
Figure 3E:
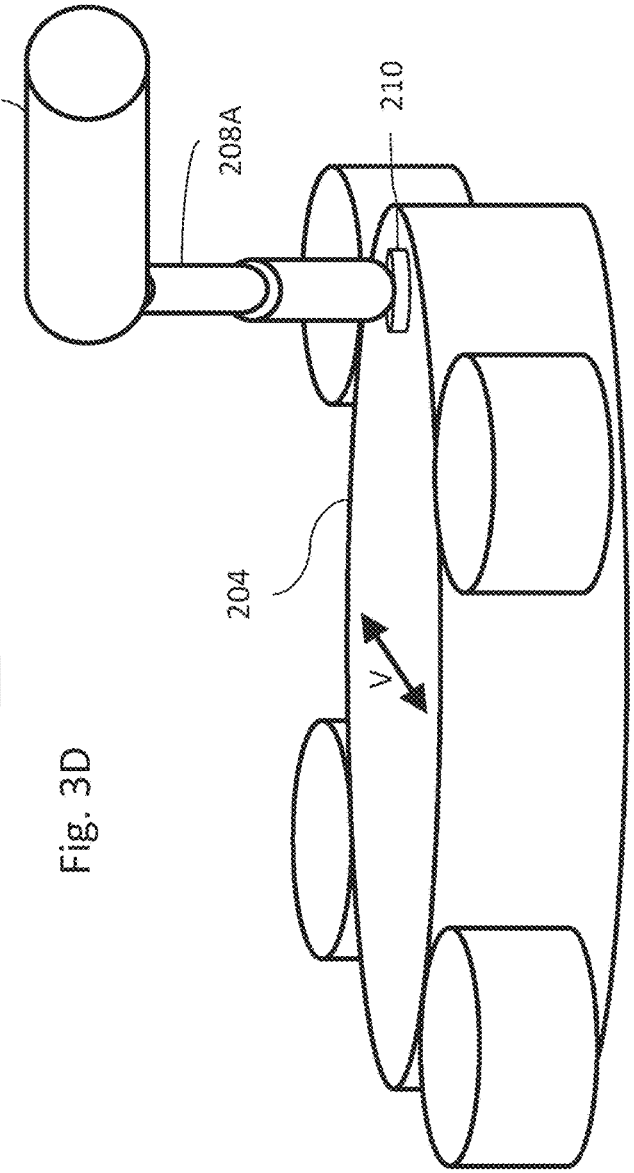

In some embodiments, the positioning assembly includes an extension arm 208 on which the optical probe is mounted. The extension arm may be rotatable or extendable, e.g. having a telescopic configuration, as shown for example in FIG. 3D. As appreciated and shown in the various figures, the extension arm may be used when the optical probe is used as a hand-held device (FIG. 3A), or mounted on a ground vehicle (FIG. 3B) or a drone (FIGS. 3B, 3D and 3E). The extension arm may be horizontally extending (as exemplified in FIGS. 3B and 3D) or vertically extending downwards or upwards (as exemplified in FIG. 3E), or incorporating or mounted on the vehicle by one or more hinges/pivots/joints 210 that enable varying and controlling the spatial orientation of the optical probe with respect to the plants by varying the angle between the extension arm and the vehicle (as exemplified in FIG. 3E) and/or between the extension arm and the optical probe and/or between different parts of the extension arm (as exemplified in FIG. 3B, a robotic arm). By this, the positioning assembly is configured and operable to facilitate imaging underside of leaves, flowers, and/or stems of fruit by the optical probe, while minimizing damage to plant parts. In order to reduce the chance for damaging leaves or fruits of the plants, the extension arm/optical probe can contain at least one flexible joint 210, which bends if forces above a predefined level are encountered. The at least one flexible joint may be located at various locations on the optical probe in order to optimize the bending force required and the time for return to normal position.

The extension arm may have a rotatable portion 208B, as exemplified in FIG. 3D, to enable rotation of the optical probe for image capture of various detected objects over a wide angular range using a single set of imaging sensor/unit, distance sensing element/unit and flash lighting element/illuminator unit. The angular rotation rate of the optical probe may be defined to compensate for the image smearing caused by relative motion between the target being imaged and the motion of the vehicle carrying the optical probe. The instantaneous rotation rate is adjusted according to the velocity of the vehicle and the distance and angle of the target from the optical probe/imaging unit. The rotation direction depends on whether the target is above or below the optical probe/imaging unit. A mesh casing or screen may be located around the rotating portion of the optical probe, where the mesh may maintain a static position in relation to the rotating portion or it may rotate together with the rotating portion.

Figure 3F:
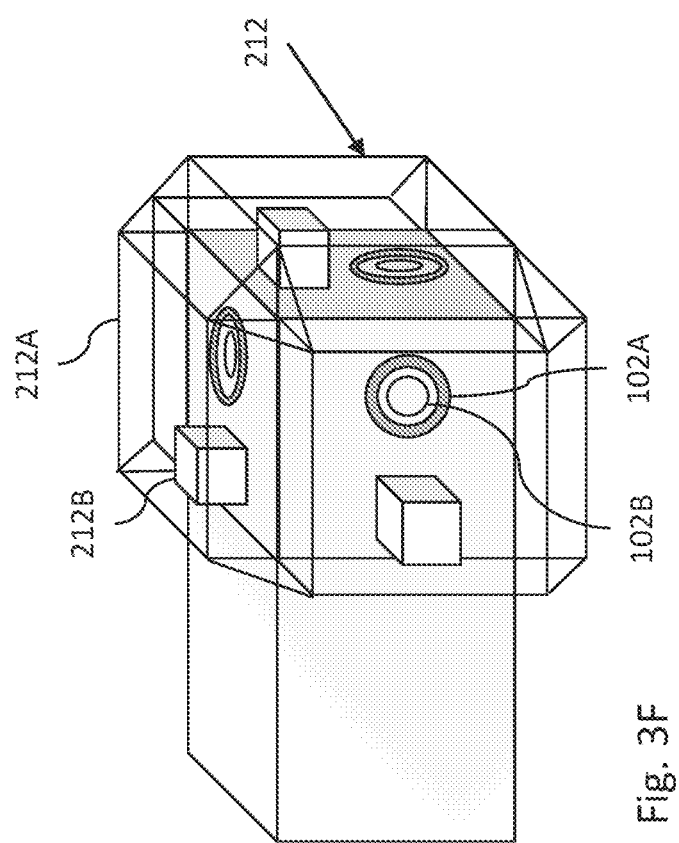

In some embodiments, as shown in FIG. 3F, the positioning assembly includes a distance controlling unit 212 comprising a distance restriction assembly 212A configured and operable to prevent the target from getting closer than a minimal focal distance of the imaging unit 102B. The distance controlling unit 212 may further include at least one sensing unit including at least one contact sensor 212B configured and operable to detect at least a partial contact between the target and distance restriction assembly 212A and generate a contact signal. The position controller 104F can be configured and operable to be responsive to the contact signal from the contact sensor to initiate the imaging session. In some embodiments, a plurality of contact sensors are provided being associated with different parts of the distance restriction assembly 212A. The position controller can be configured and operable to analyze the contact signals from the contact sensors to initiate imaging sessions using one or more respective imaging channels of the imaging unit or using one or more imaging units.

In some embodiments, as shown in FIGS. 3G1-3G3 and FIGS. 3H1 and 3H2, the positioning assembly includes a plant shifting mechanism configured and operable to shift location of plant parts with respect to path of the movement of the optical probe. In some embodiments, the plant shifting mechanism is configured and operable to shift the plant parts out of the path of movement of the optical probe. In some other embodiments, the plant shifting mechanism is configured and operable to shift the plant parts towards the optical probe during movement and bring them into the focal range of the imaging unit.

As shown in FIG. 3G1, showing a top view of the optical probe 102, a plant shifting mechanism 214 surrounds the optical probe with a space 214S therebetween, the space allows the plant shifting mechanism, at least at a portion thereof surrounding the imaging unit, to function as the distance controlling unit 212 described above and control a distance between the target and the imaging unit. A first example of the plant shifting mechanism is shown in FIG. 3G2, where the plant shifting mechanism 214 includes a first back part 214A and a second front part 214B. The back part 214A is stationary with respect to the optical probe, enabling the distance controlling function described above. The front part 214B is connected to the back part 214A via a hinge/pivot 214H and enables the front part 214B to rotate with respect to the back part 214A. The front part 214B is moveable/switchable between at least two pivotal positions, 214B1 and 214B2, with respect to the longitudinal axis of the optical probe, and by this enables shifting plant parts either out of the way or towards the imaging unit of the optical probe as the case may be. FIG. 3G3 shows a second example of the plant shifting mechanism 214, which in this example is formed from a single part 214C moveable between at least two vertical positions with respect to the optical probe and specifically with respect to the imaging unit, enabling control over the distance between the imaging unit and the imaged target, e.g. enabling bringing one plant part into focus and other plant part out of focus of the imaging unit.

As shown in FIGS. 3H1-3H2, from the side and top, the positioning assembly includes a plant shifting mechanism 214D that includes parallel slides 214D1 and 214D2 that are sloped at a leading edge of the optical probe and flattened at a distance from imaging channels of the imaging unit, where the distance is equal to a focal distance or less. This configuration enables stabilizing the leaf at a specific distance prior to passing over the distance sensing element and bringing different regions of the imaged plant part, e.g. a leaf, into focus at different times depending on the relative positioning between the optical probe and the plant part.

Targets, such as leaf underside, may be brought closer to the focal plane of the optical probe, for example by providing suction to flatten the leaf on a mesh above the optical probe, by blowing air from above or by employing a de voltage to the outside of the optical probe to create an electrostatic force to attract the leaf to the focal plane.

Figure 3I:
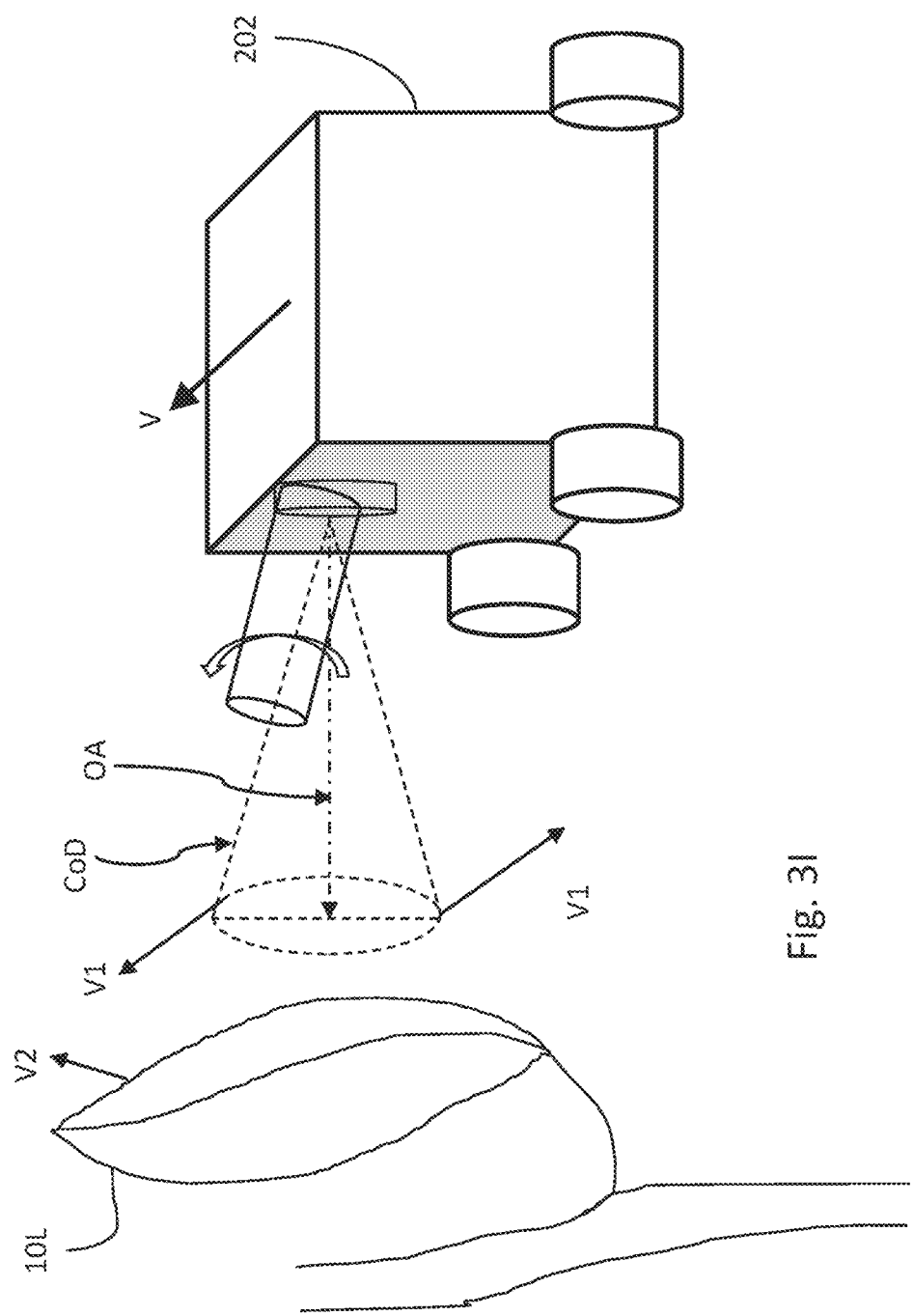

Reference is made to FIG. 3I illustrating another configuration of a positioning assembly configured and operable to reduce smearing and improve image capture while there is a relative motion between the optical probe and the plant part.

The optical probe 102 can be configured to rotate or contains a rotatable optical component/element that enables rotation of the optical axis at the object plane about a main optical axis OA, where the directions of the deflected optical axis rotate in a cone of directions CoD about the main optical axis OA. This can be useful when there is relative motion between the optical probe and plant part being imaged. The effect of the configuration described in FIG. 3I can be similar in some aspects to FIGS. 2C1 and 2C2 described above, by the ability to control the path of the optical axis of the optical probe. However, because of the positioning assembly, the embodiment described in FIG. 3I is effective also when the optical probe is accommodated in a one-piece housing that can be rotated but that does not allow differential rotation of different parts of the housing/optical probe with respect to each other. The optical axis of the optical probe can be aligned so that the vector of relative motion between the object/target and the optical probe is tangential to the conic surface and perpendicular to the optical axis when the optical axis is pointing to the object. The angular rotation rate of the rotatable optical element can be set to a value where the linear tangential velocity of the location of the optical axis at the object plane is equal in magnitude and direction to the vector of motion of the object relative to the optical probe. As shown, the optical probe is mounted on a vehicle 202 that moves forward as illustrated by the velocity vector V, typically in parallel to a row of plants to be imaged, where a leaf 10L is exemplified and which may have its own spatial movement illustrated by the vector velocity V2. The optical probe is rotated clockwise in a circular direction, such that its linear tangent velocity at each point on the circle is V1. The inspection system, through the position controller 104F can define the rotation velocity V1 based on the vectorial sum of the input motion data of the vehicle (V), the plant (V2) and the rotation velocity V1, such that the relative velocity between the optical probe and the leaf is zero, or close to zero, whenever an image is captured.

In some embodiments, the positioning assembly may contain a rotatable mirror or a prism placed on the main optical axis outside the housing of the optical probe, where the optical axis is deflected by 90 degrees to the main optical axis and where during operation an upward deflected direction of the optical axis is used to image the underside of leaves or fruit, a downward deflected direction of the optical axis is used to image the top side of leaves or fruit and a sideways deflected direction of the optical axis can be used to image stems and branches of the plant.

In some embodiments, the positioning assembly is configured and operable to rotate the optical probe/element continuously in order to compensate for image smearing during image capture by compensating for the relative motion of the plant part and optical probe.

In some embodiments, the positioning assembly is configured and operable to rotate the optical probe/element in an oscillating motion (back and forth with respect to the path of movement of the optical probe), so that it repeatedly scans a partial section of the conic surface, where it attains the correct tangential velocity of the optical axis periodically. The angular velocity of the oscillating motion may be sinusoidal, sawtooth or other periodic function.

In some embodiments, the object may be imaged asynchronously, the rotating optical probe/element may be held in a specific "standby" position, wherefrom when data about the relative motion between the optical probe and the target plant part, that can be provided by the sensing unit or the orientation imaging sensor, indicates that the target is entering the object plane after a known distance/time, a trigger signal is generated, and the rotating probe/element performs a controlled scanning motion. During the scanning motion, an image capture is performed, where the relative motion between the target and the stationary optical probe across the object plane is compensated by the controlled movement of the rotating optical probe/element.

Flash illumination may be used, in addition, to reduce the possible smearing during image capture. In some embodiments, illumination is provided at the area of the cone of directions by multiple lighting elements located around the optical probe and which are individually operated where the activated lighting element(s) are selected in accordance with the angle of the deflected optical axis. In some embodiments, multiple images are captured at a specific deflection angle position by operating different lighting elements or different subsets of lighting elements in order to achieve different angles of oblique illumination in each image.

Figures 4A, 4B:
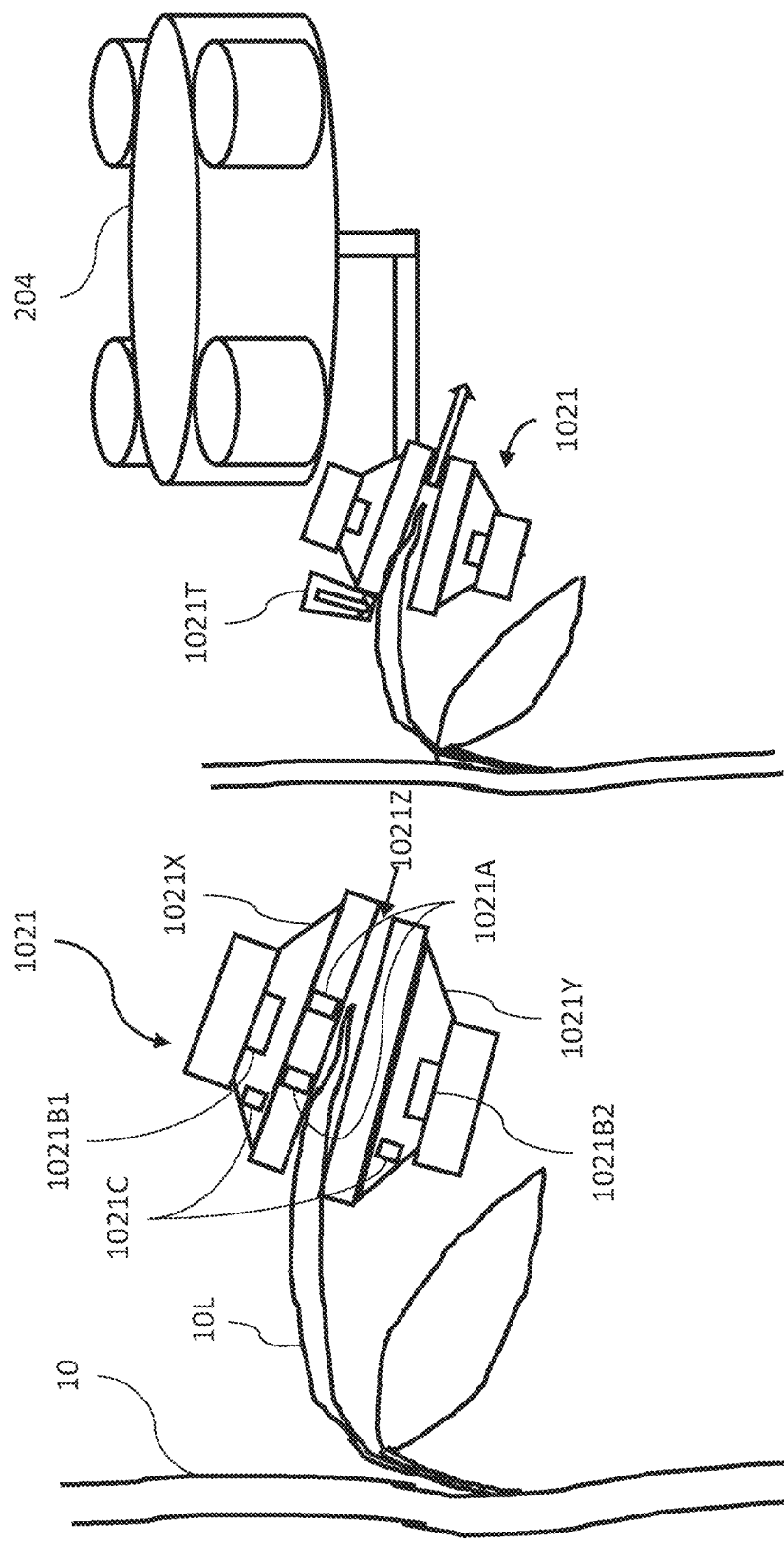

Reference is made to FIGS. 4A-4B illustrating non-limiting examples of high-resolution optical probes for facilitating and expediting capturing images of plant parts, specifically leaves, in accordance with the present invention. As shown in FIG. 4A, the optical probe 1021 is formed with two parts including a first part 1021X including a downward facing imaging unit 1021B1 and a second part 1021Y including an upward facing imaging unit 1021B2, where the focal areas of the imaging elements essentially overlap, enabling imaging of both sides of a plant leaf 10L without turning the plant leaf or without the need to access the topside and the underside of the leaf sequentially. The leaf imaging optical probe may include a sensing unit 1021C that includes one or more distance sensing elements for detecting distance between the corresponding sides of the leaf and the imaging units. In the described example, a distance sensing element is located within each part and is configured to provide distance data to the corresponding imaging unit of the respective part. The leaf imaging optical probe 1021 also includes at least one flash illuminator unit 1021A configured and operable to illuminate the plant leaf. In some embodiments, the flash illuminator unit is configured and operable to illuminate one side only of the leaf, typically by reflection illumination. In some embodiments, each part has its own flash illuminator unit configured to illuminate the respective side of the leaf, typically by reflection illumination. In some other embodiments, as illustrated in FIG. 4A, one flash illuminator unit is located within the first upper part 1021X and configured and operable to illuminate the topside of the leaf by reflection illumination and the underside of the leaf by transmission illumination. The reflection and transmission illuminations and the imaging of the topside and underside of the leaf may be done simultaneously or sequentially.

In some embodiments, the focal plane of the downward facing imaging unit is located laterally adjacent to the focal plane of the upward facing imaging unit and a leaf can be brought to the focal plane of a downward facing imaging unit sequentially to the upward facing imaging unit.

In some embodiments, the leaf imaging optical probe includes a chute 1021Z configured to receive therein the plant leaf and enable the imaging of one or both sides of the plant leaf. The leaf can be drawn into the chute by suction, airflow or mechanical rollers which are located at the edges of the chute and out of the path to the focus area.

The leaf imaging optical probe may take a series of images as the leaf slides into the chute, thus enabling covering a larger area of the leaf. The leaf imaging optical probe may include a cutter 1021T (shown for convenience in FIG. 4B, but applicable in FIG. 4A as well) for cutting off the leaf from its branch, enabling performing of the imaging of the leaf while the leaf imaging optical probe is in motion to the next target to be inspected. The cutting may be based on mechanical means (e.g. pulling the gripped leaf or cutting by a straight or v-shaped blade), electrical means (e.g. burning by arc) or optical means (e.g. burning by laser). The leaf may be expelled from the chute upon completion of the imaging. This enables increasing the time utilization efficiency of the system by utilizing travel time between targets for performing imaging and measurement operations.

As illustrated in FIG. 4B, in some embodiments, the leaf imaging optical probe is attached to a drone 204, the target leaf may be drawn in along an angled chute until it overlaps the focal area of imaging sensors of the imaging units, where the downdraft of the drone, or related suction, pulls the leaf inwards along the chute until it covers the focal area. The drone may also move towards the branch holding the leaf, aiding the ingress of the leaf into the chute of the leaf imaging optical probe.

As illustrated in FIGS. 4C1-4C2, in some embodiments, the leaf imaging optical probe may include one or more of the following: a leaf holder 230 for holding the leaf in a static position with respect to the imaging units, an assembly for guiding the leaf to the focal area (231A, 231B), an assembly for cutting the plant branch (a branch cutter) 233 and an assembly for flattening the leaf and holding it near the optical focal area (a leaf flattener) 232. The leaf guiding assembly may contain cylindrical rolling elements (231A, 231B) on the bottom and/or top side of the leaf enabling control of various leaf shapes of various types of plants. The rolling elements are spaced-apart with an adjustable gap to prevent damage to the leaves. The leaf flattener 232 may be passively positioned or may be adjusted actively based on information about the leaf position provided by the sensing unit 1021C. The flattener is located at the focal plan of at least one imaging unit (e.g. 1021B) and is illuminated by at least one flash illuminator unit (e.g. 1021A). A laterally facing or forward-facing orientation imaging sensor 206 may also be used to recognize the position and angle of the target leaf and guide the vehicle to capture the edge of the leaf and draw it in to the opening of the leaf imaging optical probe.

As illustrated in FIGS. 4D1-4D3, the entrance to the leaf imaging optical probe may be forward-facing (parallel) to the direction of travel and parallel to rows of plants. Thus, the direction of leaf capture and scanning is parallel to the direction of travel. The leaf imaging optical probe may include the assemblies described above with reference to FIGS. 4C1-4C2 and which are annotated with the same reference numbers. This configuration of the leaf imaging optical probe enables capturing, sampling and expelling leaves while maintaining forward motion of the vehicle. The drone 204 in FIG. 4D1 is shown as a non-limiting example of a vehicle that can also be a ground vehicle.

The leaf imaging optical probe may be designed in accordance with the species of plant being inspected. In this case, the customized mechanisms are designed to match leaves of a plant according to the size, shape, stiffness, thickness of leaves as well as leaf spacing, leaf angle and leaf location on branches. The location of the imaging sensor(s) focal area may be optimized for resolution, field of view and depth of focus for the typical types and locations of pests and diseases of the plant species.

The inspection system of the present invention can include an image processor and analyzer, e.g. the image analyzer 104G, for processing of the captured images, either immediately during an imaging session or after finishing the imaging session(s). Additionally or alternatively, the inspection system may be configured and operable to communicate with an external image processor and analyzer to send raw image data thereto and receive analyzed images aiding in planning the next imaging sessions. The image processor and analyzer can be integrated with the optical probe or the control unit, or be located in a separate utility. The inspection system may be configured and operable to capture multiple images with a shift in focus distance between them. The image processor and analyzer (either internal or external) detects the areas in each image that are in focus and merges all the in-focus areas into a single image. Flash illumination may be operated to reduce the motion blurring in each image during capture. The image processor and analyzer may refrain from utilizing one or more images out of the multiple images if it is found, by the analysis, that the blur of the specific image is larger than a predefined threshold. Due to possible relative motion between the target and the optical probe, the order of focus distance may change, therefore the image processor and analyzer can detect the areas in focus and arrange the in-focus zones on the final image accordingly in a non-sequential manner. For each image used in the focus stacking, details can be recorded enabling calculation of the optical magnification at the focal plane, for example the distance between the back and front principle planes and their respective focal points. The image data is used to correct the magnification and distortion of each image prior to combining the images.

In some embodiments, the system is configured to utilize the relative motion between the optical unit and the target having a certain depth profile to generate multiple images of the target with different focus conditions covering the whole depth of the target. When approaching a target in an essentially perpendicular direction to the target, the inspection system, specifically the position controller 104F, receiving input position data from a sensor such as the distance sensing element(s) or orientation image sensor, can determine distance pitches at which the imaging unit is to be operated during motion in a multiple image capture sequence where the axial distance pitches between the image captures is determined in relation to the depth of focus of the imaging unit. For example, if the target has a depth Y and the imaging unit has a depth of focus of Y/n, then n in-focus images covering the depth Y should be captured. Controlling the distances between the image captures along the axial direction, being the direction of the relative motion between the imaging unit and the target, or controlling the speed of the relative motion insures that the whole depth of the target will be imaged. In other words, the relative position of the first and final images of the sequence can be defined to enable image capture of the full depth of the object.

In some embodiments, the multiple images are not combined into a single image. Instead, only the in-focus objects in each image are selected and combined onto a plane where all other areas are omitted. The resulting image contains all objects of interest within the volume scanned during the multiple image capture but may contain empty areas.

The threshold for selecting an object as being in-focus may be varied and adjusted based on a learning phase. If a certain object is selected in more than one image, a contrast comparison can be used to remove the less focused version.

In some embodiments, multiple images can be captured, each with a different azimuthal angle of illumination relative to the optical axis at the image plane. This can enable enhancing the contrast of small objects on the surface of the plant.

In the case where the object plane is not perpendicular to the optical axis, illuminating with an off-axis source closer to perpendicularity with the tilted object plane can enhance the illumination uniformity, while reducing energy use of the non-operating sources. Additionally, location of the illumination lighting element relative to the optical probe may be adjusted to optimize the light concentration on the target.

If the required object is a fruit with shiny surface, then the illumination may be operated via a diffusive surface in order to reduce bright spots from specular reflection.

The working distance of the illumination to the object plane may be large relative to the diameter of the imaged object plane. Collimation or even reduction in the diameter of the illumination beam, may achieve high light concentration at the object plane. In one embodiment, the light concentration may be achieved by a cylindrical tube or conical tube with a reflective inner surface placed around the optical axis.

The optical probe and the leaf imaging optical probe can be designed for easy decontamination and/or replacement of parts that come into contact with the plants. The decontamination could be performed by an additional service vehicle that periodically meets the vehicle during operations. Alternatively, the decontamination can be performed by the vehicle itself, for example by electrostatic charging, vibration or by heating of surfaces.

Any part of the inspection system which may come into contact with the plants may be coated with material, such as Teflon, nano-structured or other coatings, that reduces adhesion of contamination and particles to the surface.

In some embodiments, the optical probe can be inserted by the vehicle into a decontamination system during flight. In a specific embodiment, the optical probe can by lowered into a downward pointing vertical position and immersed in at least one liquid decontamination solution.

The invention claimed is:

1. An inspection system for use in monitoring plants' conditions in a plant growing area, the inspection system comprises:
    an optical probe comprising at least one imaging set, each imaging set comprising: a flash illuminator unit; an imaging unit configured with a predetermined resolution; and a sensing unit; the optical probe being configured and operable to perform one or more imaging sessions on a target in a plant growing area at a target location during a movement of the optical probe along a movement path in a vicinity of the target location, said sensing unit comprising a distance sensing element configured and operable to determine an instantaneous distance between the imaging unit and the target being imaged, and generate distance sensing data indicative thereof; and a control unit configured and operable to be responsive to the distance sensing data to initiate the imaging session and synchronize operation of the flash illuminator unit and the imaging unit to capture images of the target by the optical probe, thereby enabling analyzing the images and determining a condition of the target being indicative of at least one of pest, insect and disease presence at the target;

wherein said sensing unit is located a predetermined distance before said imaging unit with respect to the movement path of the optical probe, and the control unit is configured and operable to utilize data indicative of velocity of said movement along the movement path, and determine a time passing between time of detection of the target by the sensing unit and the time at which the imaging session is to be initiated to thereby timely activate the flash illuminator unit and the imaging unit.

2. The inspection system according to claim 1, wherein said predetermined resolution of the imaging unit provides a spatial resolution of the imaging unit in an object plane in a range of 1-100 microns.

3. The inspection system according to claim 1, characterized by at least one of the following:

said sensing unit comprises a plurality of distance sensing elements arranged in a spaced-apart relationship on a sensing surface having a predetermined geometry, each of the distance sensing elements providing distance data indicative of a distance from said distance sensing element to the target location, the distance sensing data provided by the sensing unit being therefore indicative of a plane or volume map of the vicinity of the target location depending on the geometry of said sensing surface;

said sensing unit comprises a one-dimensional array of distance sensing elements arranged transversely to the movement path of the optical probe and said imaging unit defines a two-dimensional array of imaging channels such that each distance sensing element is associated with a one-dimensional array of the imaging channels arranged in a spaced-apart relationship along the movement path of the optical probe.

4. The inspection system according to claim 1, wherein said imaging unit has at least one of the following configurations:

defines a plurality of different imaging channels having different focal conditions, or defines at least one imaging channel configured with an adaptive focal condition within said focal range for imaging along said at least one imaging channel;

the imaging unit being thereby configured and operable to acquire a plurality of images with different focal conditions within the focal range of the imaging unit during said imaging sessions, the distance sensing data being indicative of the distance between each of imaging channel and the target to be imaged.

5. The inspection system according to claim 4, wherein said imaging unit defines at least one imaging channel configured with an adaptive focal condition within said focal range for imaging along said at least one imaging channel, the control unit being configured and operable to determine the focal condition based on said distance sensing data being indicative of the distance between the imaging unit and the target and controllably operate the imaging unit to successively perform the imaging sessions with the different focal conditions.

6. The inspection system according to claim 4, wherein said imaging unit defines the plurality of different imaging channels, the control unit being configured and operable to determine a time sequence of operation of the flash illuminator unit and operation of the imaging unit with the different focal conditions based on one or more of the following: the focal conditions, the movement of the optical probe, and said distance sensing data, to thereby obtain the plurality of images.

7. The inspection system according to claim 6, wherein said control unit has one of the following configurations:

the control unit is configured to spatially divide the target into one or more sections and allocate one or more imaging channels for imaging each of said one or more sections; and the control unit is configured to spatially divide the target into one or more sections and allocate a number of the imaging channels for imaging each of said one or more sections, such that fields of view of the imaging channels in each section either overlap or are shifted along the movement path of the optical probe, the plurality of images thereby covering the whole target.

8. The inspection system according to claim 1, wherein said flash illuminator unit comprises one or more lighting elements associated with each imaging channel defined by the imaging unit, each of said one or more lighting elements, associated with each imaging channel, being arranged with a different angular orientation with respect to an optical axis of the imaging channel, said control unit being configured and operable to determine an angle between the target location and the optical axis of the imaging channel, and select, for each imaging session, one or more of said one or more lighting elements to provide uniform illumination of the target.

9. The inspection system according to claim 1, wherein said control unit further comprises a flash controller configured and operable to control at least one of illumination intensity, illumination angle and illumination time pattern of said flash illuminator unit, based on one or more of the following: input motion data indicative of the movement path of the optical probe in the vicinity of the target location, number of lighting elements of the flash illuminator unit, distance of a focal plane, exposure time, ambient light, an angle between the target and the flash illuminator unit, reflectivity of target, type of the target, and type of a part of the target being imaged.

10. The inspection system according to claim 9, further comprising a movement detection unit configured and operable for providing input motion data to control the imaging sessions and a time sequence of operation of the flash illuminator unit and of the different imaging channels.

11. The inspection system according to claim 1, wherein the optical probe has at least one of the following configurations:

the optical probe comprises a housing containing the flash illuminator unit, the imaging unit, and the sensing unit, said housing comprising a portion thereof formed with at least one mesh screen comprising an array of features arranged substantially parallel to the movement path of the optical probe, or at least one optical window aligned with a respective at least one imaging channel defined by the imaging unit, to thereby enable imaging of the target via said at least one mesh screen or said optical window;

the optical probe further comprises at least one light directing element associated with a respective at least one imaging channel defined by the imaging unit, for collecting input light from the target and directing collected light to propagate along said imaging channel to a detector of the imaging unit, the at least one lighting element being positioned upstream of the light directing element with respect to a direction of propagation of the input light;

the optical probe comprises a plurality of the imaging sets, each imaging set being configured with a field of view of a different angular orientation with respect to an axis of the optical probe.

12. The inspection system according to claim 1, further comprising at least one of the following:

an indication unit configured and operable to provide indication about an operational state of the optical probe;

a position controller configured and operable to control one or more of the following: a position of the optical probe, an orientation of the optical probe, an orientation of the movement path of the optical probe with respect to said target location, based on input position data;

at least one additional imaging unit configured for defining one or more measurement channels, for performing at least one of spectrophotometry, multi-spectral and UV-fluorescence measurements;

a distance controlling unit comprising a distance restriction assembly configured and operable to prevent the target from getting closer than a minimal focal distance of the imaging unit;

a positioning assembly configured and operable to control the movement path of the optical probe in the vicinity of the target and adjust a position of the optical probe with respect to said target location, to enable one or more of the following: imaging underside, upper side or side of a plant part by the imaging unit, and reduce image smearing and blur during relative motion between the optical probe and the target;

a plant shifting mechanism configured and operable to shift at least a part of the target with respect to the movement path of the optical probe;

an image analyzer configured and operable to carry out at least one of the following: detect in-focus portions in each of a plurality of images acquired by the imaging unit and merge the in-focus portions into a single in-focus image of the target;

detect optimally-illuminated portions in the plurality of images, being acquired with different imaging conditions including at least one of an illumination intensity and illumination angle, and merge the optimally illuminated portions into a single image of the target.

13. The inspection system according to claim 1, further comprising a position controller configured and operable to control one or more of the following: a position of the optical probe, an orientation of the optical probe, an orientation of the movement path of the optical probe with respect to said target location, based on input position data, the position controller being configured and operable to carry out at least one of the following: to communicate with an external information source to receive said input position data; and to access said input position data stored in a database of an inspection history.

14. The inspection system according to claim 1, further comprising a position controller configured and operable to control one or more of the following: a position of the optical probe, an orientation of the optical probe, an orientation of the movement path of the optical probe with respect to said target location, based on input position data, wherein said target has a certain depth profile, said imaging unit having a certain depth of focus smaller than a depth of the target, and said position controller being configured and operable to determine a pitch distance, along the movement path, between consecutive plurality of images being acquired by the imaging unit, and control the motion and image acquisition of the imaging unit to capture the plurality of images such that each image is acquired at a different location along the depth profile of the target, thereby enabling generating focused images of the target along the whole depth of the target.

15. The inspection system according to claim 1, further comprising a distance controlling unit comprising a distance restriction assembly configured and operable to prevent the target from getting closer than a minimal focal distance of the imaging unit, wherein said distance controlling unit has one of the following configurations:

the distance controlling unit comprises at least one contact sensor configured and operable to detect at least a partial contact between the target and the distance restriction assembly and generate a contact signal indicative of the at least partial contact, wherein said control unit comprises a position controller configured and operable to be responsive to said contact signal to initiate the imaging session;

the distance controlling unit comprises a plurality of contact sensors associated with different parts of the distance restriction assembly, each of the contact sensors being configured and operable to detect at least a partial contact between the target and the respective part of the distance restriction assembly and generate a respective contact signal indicative of the at least partial contact, said position controller of the control unit being configured and operable to analyze the contact signals from the contact sensors to initiate imaging sessions using one or more respective imaging channels of the imaging unit.

16. The inspection system according to claim 1, comprising a positioning assembly configured and operable to control the movement path of the optical probe in the vicinity of the target and adjust a position of the optical probe with respect to said target location, to enable one or more of the following: imaging underside, upper side or side of a plant part by the imaging unit, and reduce image smearing and blur during relative motion between the optical probe and the target.

17. The inspection system according to claim 16, wherein said positioning assembly comprises an orientation imaging sensor configured and operable to provide path data indicative of one or more obstacles or target parts located in the movement path of the optical probe said control unit being configured and operable to receive and analyze said path data, and selectively carry out at least one of the following: upon identifying the target parts in the path data, control the movement path of the optical probe in order to bring the target parts into the focal range of the imaging unit, and upon identifying one or more of the obstacles in the path data control the movement path of the optical probe in order to prevent collision of the optical probe with the obstacles.

18. The inspection system according to claim 16, wherein said positioning assembly comprises an orientation imaging sensor configured and operable to provide path data indicative of one or more obstacles or target parts located in the movement path of the optical probe, said control unit being configured and operable to receive and analyze said path data to enable selecting the target to be imaged.

19. The inspection system according to claim 1, comprising a plant shifting mechanism configured and operable to shift at least a part of the target with respect to the movement path of the optical probe, wherein said plant shifting mechanism is configured and operable to selectively carry out at least one of the following: shift said at least part of the target out of the movement path of the optical probe; and shift said at least part of the target towards the optical probe during movement and bring said plant part into the focal range of the imaging unit.

20. The inspection system according to claim 19, wherein said plant shifting mechanism comprises parallel slides that are sloped at a leading edge of the optical probe and flattened at a distance from imaging channels of the imaging unit not exceeding a focal distance of the imaging unit.

21. The inspection system according to claim 1, wherein said imaging unit comprises a leaf imaging optical probe having at least one of the following configurations: the leaf imaging optical probe comprising a downward facing imaging element and an upward facing imaging element, whereby fields of view of the imaging elements essentially overlap, enabling imaging of both sides of a plant leaf without turning the plant leaf; and the leaf imaging optical probe comprising at least one flash illuminator element configured and operable to illuminate both sides of the plant leaf, and wherein reflected light imaging is performed on one side of the leaf either simultaneously or sequentially with transmitted light imaging on the second side of the leaf.

22. The inspection system according to claim 21, characterized by at least one of the following:
the system further comprises a chute configured to receive therein the plant leaf and enable said imaging of at least one side of the plant leaf by the leaf imaging optical probe;
the system further comprises a purifier device configured and operable to decontaminate the optical probe utilizing one or more of the following: heat, electrostatic electricity, vibration and or immersion in a purifying compound;
said leaf imaging optical probe comprises one or more of the following: a leaf holder assembly, a leaf guiding assembly, a leaf flattener assembly, and a leaf cutter assembly.

23. The inspection system according to claim 1, wherein having at least one of the following configurations:
said imaging unit is configured to capture a plurality of images of the target, each of the images with a different focal condition, the inspection system further comprising an image analyzer configured and operable to detect in-focus portions in each of the plurality of images and merge the in-focus portions into a single in-focus image of the target;
said imaging unit is configured to acquire a plurality of images of the target, each of the images being acquired with different imaging conditions including at least one of an illumination intensity and illumination angle, the inspection system further comprising an image analyzer configured and operable to detect optimally-illuminated portions in the plurality of images and merge the optimally illuminated portions into a single image of the target.

24. The inspection system according to claim 1, comprising a positioning assembly configured and operable to cause continuous or intermittent movement of an optical axis of the optical probe to compensate for a relative motion between the optical probe and the target.

25. The inspection system according to claim 24, wherein said positioning assembly is configured and operable to carry out one of the following:
rotate the optical axis of the optical probe such that the optical axis scans around a conic surface, where a vector of the relative motion between the target and the optical probe is tangential to a base of the conic surface and is substantially equal to a vector of the movement of the optical axis when the optical axis points to the target;
oscillate said optical axis of the optical probe along an oscillation path, where a vector of the relative motion between the target and the optical probe is tangential to at a least a portion of the oscillation path and is substantially equal to a vector of the movement of the optical axis when the optical axis points to the target; and
maintain said optical axis of the optical probe in a stationary position during the relative motion between the optical probe and the target, and, in response to data indicative of a condition that the target is entering an object plane of the imaging unit, controllably move the optical axis such that the relative motion between the target and the optical axis across the object plane is compensated and an image of the target is acquired.

26. The inspection system according to claim 1, configured as a hand-held device, wherein said hand-held device has one of the following configurations: (i) the hand-held device comprises a common housing carrying said optical probe and said control unit; and (ii) the hand-held device is configured as a two-part unit carrying the optical probe and the control unit in respective first and second unit parts configured to be connected to one another.

27. A vehicle carrying the inspection system of claim 1, said vehicle being configured as a ground vehicle or as a flying platform.

28. The inspection system according to claim 1, wherein the imaging unit has at least one of the following configurations:
defines a plurality of different imaging channels having different focal conditions, or defines at least one imaging channel configured with an adaptive focal condition within said focal range for imaging along said at least one imaging channel; the imaging unit being thereby configured and operable to acquire a plurality of images with different focal conditions within the focal range of the imaging unit, the distance sensing data being indicative of the distance between each of imaging channel and the target to be imaged; and
wherein the control unit comprises an image controller configured and operable to determine the focal condition based on said distance sensing data and controllably operate the imaging unit to successively perform the imaging sessions with different focal conditions, the control unit being configured to determine a time sequence of operation of the flash illuminator unit and operation of the imaging unit with the different focal conditions based on one or more of the following: the focal conditions, the movement of the optical probe, and said distance sensing data, to thereby obtain the plurality of images.

29. An inspection system for use in monitoring plants' conditions in a plant growing area, the inspection system comprises:

an optical probe comprising at least one imaging set, each imaging set comprising: a flash illuminator unit; an imaging unit configured with a predetermined resolution; and a sensing unit; the optical probe being configured and operable to perform one or more imaging sessions on a target in a plant growing area at a target location during a movement of the optical probe along a movement path in a vicinity of the target location, said sensing unit comprising a distance sensing element configured and operable to determine an instantaneous distance between the imaging unit and the target being imaged, and generate distance sensing data indicative thereof; and a control unit configured and operable to be responsive to the distance sensing data to initiate the imaging session and synchronize operation of the flash illuminator unit and the imaging unit to capture images of the target by the optical probe, thereby enabling analyzing the images and determining a condition of the target being indicative of at least one of pest, insect and disease presence at the target;

wherein said sensing unit comprises a one-dimensional array of distance sensing elements arranged transversely to the movement path of the optical probe and said imaging unit defines a two-dimensional array of imaging channels such that each distance sensing element is associated with a one-dimensional array of the imaging channels arranged in a spaced-apart relationship along the movement path of the optical probe.

30. An inspection system for use in monitoring plants' conditions in a plant growing area, the inspection system comprises:

an optical probe comprising at least one imaging set, each imaging set comprising: a flash illuminator unit; an imaging unit configured with a predetermined resolution; and a sensing unit; the optical probe being configured and operable to perform one or more imaging sessions on a target in a plant growing area at a target location during a movement of the optical probe along a movement path in a vicinity of the target location, said sensing unit comprising a distance sensing element configured and operable to determine an instantaneous distance between the imaging unit and the target being imaged, and generate distance sensing data indicative thereof;

a control unit configured and operable to be responsive to the distance sensing data to initiate the imaging session and synchronize operation of the flash illuminator unit and the imaging unit to capture images of the target by the optical probe, thereby enabling analyzing the images and determining a condition of the target being indicative of at least one of pest, insect and disease presence at the target; and a plant shifting mechanism comprising parallel slides that are sloped at a leading edge of the optical probe and flattened at a distance from imaging channels of the imaging unit not exceeding a focal distance of the imaging unit, the plant shifting mechanism being configured and operable to shift at least a part of the target with respect to the movement path of the optical probe, and to selectively carry out at least one of the following: shift said at least part of the target out of the movement path of the optical probe; and shift said at least part of the target towards the optical probe during movement and bring said plant part into the focal range of the imaging unit.

31. An inspection system for use in monitoring plants' conditions in a plant growing area, the inspection system comprises:

an optical probe comprising at least one imaging set, each imaging set comprising: a flash illuminator unit; an imaging unit configured with a predetermined resolution; and a sensing unit; the optical probe being configured and operable to perform one or more imaging sessions on a target in a plant growing area at a target location during a movement of the optical probe along a movement path in a vicinity of the target location, said sensing unit comprising a distance sensing element configured and operable to determine an instantaneous distance between the imaging unit and the target being imaged, and generate distance sensing data indicative thereof; and a control unit configured and operable to be responsive to the distance sensing data to initiate the imaging session and synchronize operation of the flash illuminator unit and the imaging unit to capture images of the target by the optical probe, thereby enabling analyzing the images and determining a condition of the target being indicative of at least one of pest, insect and disease presence at the target;

wherein said imaging unit comprises a leaf imaging optical probe having at least one of the following configurations: the leaf imaging optical probe comprising a downward facing imaging element and an upward facing imaging element, whereby fields of view of the imaging elements essentially overlap, enabling imaging of both sides of a plant leaf without turning the plant leaf; and the leaf imaging optical probe comprising at least one flash illuminator element configured and operable to illuminate both sides of the plant leaf, and wherein reflected light imaging is performed on one side of the leaf either simultaneously or sequentially with transmitted light imaging on the second side of the leaf.

* * * * *